United States Patent
Kayyali et al.

(10) Patent No.: US 9,615,773 B1
(45) Date of Patent: Apr. 11, 2017

(54) METHOD AND DEVICE FOR SLEEP ANALYSIS AND THERAPY

(75) Inventors: Hani Kayyali, Shaker Heights, OH (US); Brian M. Kolkowski, Leroy, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 2685 days.

(21) Appl. No.: 12/228,462

(22) Filed: Aug. 13, 2008

(51) Int. Cl.
*A61B 5/08* (2006.01)
*A61B 5/103* (2006.01)

(52) U.S. Cl.
CPC .............. *A61B 5/08* (2013.01); *A61B 5/103* (2013.01)

(58) Field of Classification Search
None
See application file for complete search history.

(56) References Cited

U.S. PATENT DOCUMENTS

| | | | |
|---|---|---|---|
| 5,353,788 A * | 10/1994 | Miles | 128/204.23 |
| 5,666,960 A | 9/1997 | Fredberg et al. | |
| 5,704,345 A | 1/1998 | Berthon-Jones | |
| 5,882,314 A | 3/1999 | Fredberg et al. | |
| 5,902,237 A | 5/1999 | Glass | |
| 5,902,250 A * | 5/1999 | Verrier et al. | 600/515 |
| 6,142,952 A | 11/2000 | Behbehani et al. | |
| 6,159,158 A * | 12/2000 | Lowe | 600/529 |
| 6,212,435 B1 * | 4/2001 | Lattner et al. | 607/134 |
| 6,379,311 B1 | 4/2002 | Gaumond et al. | |
| 6,435,182 B1 * | 8/2002 | Lutchen et al. | 128/204.21 |
| 6,440,083 B1 | 8/2002 | Fredberg et al. | |
| 6,443,907 B1 | 9/2002 | Mansy et al. | |
| 6,450,957 B1 * | 9/2002 | Yoshimi et al. | 600/309 |
| 6,709,404 B1 | 3/2004 | Creedon et al. | |
| 7,794,399 B2 | 9/2010 | Singh | |
| 2002/0193697 A1 * | 12/2002 | Cho et al. | 600/529 |
| 2003/0199945 A1 * | 10/2003 | Ciulla | 607/48 |
| 2004/0210153 A1 * | 10/2004 | Tsukashima et al. | 600/532 |
| 2005/0081847 A1 * | 4/2005 | Lee et al. | 128/200.24 |
| 2005/0101843 A1 * | 5/2005 | Quinn et al. | 600/300 |
| 2005/0154303 A1 * | 7/2005 | Walker et al. | 600/443 |
| 2005/0197588 A1 * | 9/2005 | Freeberg | 600/529 |
| 2006/0037615 A1 * | 2/2006 | Wilkinson et al. | 128/204.23 |
| 2006/0241510 A1 * | 10/2006 | Halperin et al. | 600/534 |
| 2007/0162085 A1 * | 7/2007 | DiLorenzo | 607/40 |
| 2007/0239056 A1 | 10/2007 | Moore | |
| 2008/0033303 A1 * | 2/2008 | Wariar et al. | 600/483 |
| 2011/0066058 A1 | 3/2011 | Singh | |

* cited by examiner

*Primary Examiner* — Mark Shibuya
*Assistant Examiner* — Richard Moerschell
(74) *Attorney, Agent, or Firm* — Brian Kolkowski

(57) ABSTRACT

The present invention is related to a device and method for improvement of sleep testing and sleep therapy using acoustic data to examine various aspects of a subject's sleep quality. More particularly, the method and device of the present invention includes the use of an acoustic actuator and an acoustic sensor to acoustically monitor the state of a subject's airway during sleep in order to determine airway obstructions and their locations as they relate to, among other variables, a subject's sleep stage, body position and sleep quality.

13 Claims, 14 Drawing Sheets

METHOD AND DEVICE FOR SLEEP ANALYSIS AND THERAPY

BACKGROUND OF THE INVENTION

1. Field of Use

The present invention is related to a device and method for improvement of sleep testing and sleep therapy using acoustic diagnostic methods to examine various aspects of a subject's sleep quality. More particularly, the method and device of the present invention includes the use of an acoustic actuator and an acoustic sensor to acoustically monitor the state of a subject's airway during sleep in order to determine airway obstructions and their locations as they relate to a subject's sleep stage, body position and sleep quality.

2. Technology Review

Nearly one in seven people in the United States suffer from some type of chronic sleep disorder, and only 50% of people are estimated to get the recommended seven to eight hours of sleep each night. It is further estimated that sleep deprivation and its associated medical and social costs (loss of productivity, industrial accidents, etc.) exceed $150 billion per year. Excessive sleepiness can deteriorate quality of life and is a major cause of morbidity and mortality due to its role in industrial and transportation accidents. Sleepiness further has undesirable effects on motor vehicle operation, employment, higher earning and job promotion opportunities, education, recreation, and personal life.

Primary sleep disorders affect approximately 50 million Americans of all ages and include narcolepsy, restless legs/periodic leg movement, insomnia, and, most commonly, obstructive sleep apnea (OSA). OSA's prevalence in society is comparable to that of diabetes, asthma, and the lifetime risk of colon cancer. OSA is grossly under diagnosed with an estimated 80-90% of persons afflicted having not received a clinical diagnosis.

Although various methods exist to diagnose sleep disorders, the most common method of diagnosis of primary sleep disorders is the use of sleep testing. Sleep testing, or conducting a sleep study, involves the use of a combination of sensors and various physiological measurements to examine a subject's sleep health. In its simplest form, sleep testing can consist of the use of a single sensor to monitor a subject's sleep quality. More commonly, sleep testing is conducted using at least three sensors for measuring respiratory effort, heart rate, and blood oxygen saturation. In more complex forms, sleep testing can include the addition of sensors for measuring brain activity, airflow and muscle activity. One example of this is all-night polysomnography (PSG) which includes the use of brain and muscle activity measurements to perform sleep staging during a sleep study.

Notwithstanding the many types of sensors commonly used to monitor physical and physiological variables during a sleep study, currently, no viable methods exist to accurately and conveniently localize the location of airway obstructions while a subject sleeps during a sleep test or sleep therapy procedure. Although a number of airway imaging modalities exist, including cephalometry, computed tomography and pharyngometry, these cannot practically be used while a subject sleeps because of the nature of the equipment required to perform these procedures. Other imaging methods, such as sleep endoscopy and esophageal manometry, may be used while a subject sleeps, but are costly, ineffective and invasive, as they require placement of nasal catheters or endoscopes into the pharynx of a subject under local anesthetic for prolonged periods of time, and positioning of the patient. These procedures are thus used on a limited basis and are not in practice correlated with other parameters related to sleep quality.

To address these shortcomings, it is therefore an object of the present invention to provide a device and method for convenient, non-invasive monitoring of airway state while a subject sleeps during sleep testing and sleep therapy procedures. It is another object of the present invention to provide a method and device wherein an acoustic generator and acoustic sensor placed near the mouth of a subject collect information on the nature and location of obstructive tissue within a subject's airway. It is another object of the present invention to provide a method and device by which information pertaining to the nature and location of obstructive tissue within a subject's airway is used in surgical planning to determine the tissue to be removed or extracted during surgery. It is still another object of the present invention to provide a method and device wherein information pertaining to the nature and location of obstructive tissue within a subject's airway is used to modulate a positive airway pressure device during positive airway pressure therapeutic and diagnostic procedures. It is still another object of the present invention to correlate obstruction location with other sensors used to determine sleep quality to better understand the basis for the obstruction. It is still another object of the present invention to use location or size of obstruction information to titrate treatment of the subject.

SUMMARY OF THE INVENTION

The present invention is both a device and a method for improvement of sleep testing and sleep therapy using acoustic data to examine certain aspects of a subject's sleep quality. More particularly, the method and device of the present invention can be used to acoustically monitor the state of a subject's airway during sleep. The present invention is further related to the devices and sensors used in executing the method, and includes various embodiments of a method of inpatient and remote sleep analysis.

The device and method of the present invention is particularly useful in a number of applications. These applications include, but are not limited to, testing and/or treating a subject with a sleep disorder, more particularly an obstructive respiratory sleep disorder. The device and method of the present invention is further particularly useful when conducting sleep testing and analysis wherein acoustic data pertaining to the state of a subject's airway is used to diagnose a subject's sleeping disorder. A further application is for use in tritrating the subject's treatment. A still further useful application of the device and method of the present invention is the use of acoustic data to localize an airway obstruction in a subject with a sleep disorder and using this data, at least in part, in determining tissue to be surgically removed from a subject's airway. The device and method of the present invention includes any useful applications not listed, which will be apparent to those skilled in the art.

The device and method of the present invention provides a sensor and accuator to acoustically monitor the state of a subject's airway during sleep. Numerous methods are disclosed herein to conduct acoustic monitoring of a subject's airway during sleep testing and sleep therapy procedures. Among the methods disclosed is the use of an acoustic transducer placed in a mask near the mouth of the subject to both generate and record acoustic data. Also disclosed are methods of using acoustic data collected with an acoustic transducer to determine, at least in part, effectiveness of various sleep disorder treatment options. Other methods disclosed in the present invention include correlation of physiologic, kinetic and acoustic parameters pertaining to a subject's sleep quality to determine, in greater detail, the nature of a subject's sleep disorder. Still other methods exist, many of which will be clear combinations of the steps disclosed herein.

The device and method for example provides a method of correlation of acoustic data with positive airway pressure supplied by a positive airway pressure device. This method looks at the effect of treatment under various subject conditions to determine the optimal method of adjusting or setting the treatment device. To this end, the device and method includes means whereby acoustic data can be analyzed and used to communicate a desired pressure output to a positive airway pressure device. Of particular interest, the method and device looks at airway obstructions with respect to body position, sleep stage of the subject, during respiratory events, and based on treatment ranges, i.e., PAP pressure or airflow.

Examples of various embodiments of the present invention are as follows: In one embodiment, the present invention includes the use of a method of diagnosing and treating sleep related airway obstructions of a subject comprising the steps of conducting a sleep test using a data acquisition system comprising at least one actuator and at least one sensor, the at least one actuator being an acoustic generator and the at least one sensor being an acoustic sensor, the sleep test comprising the step of measuring or estimating a subject's airway for obstruction(s) during sleep with both the at least one actuator and at least one sensor of the data acquisition system, using the measured or estimated obstruction(s) in the subject's airway determined during the sleep test, at least in part, to make a determination of tissue to be removed or extracted during surgery, and performing surgery to remove, at least in part, the obstruction(s) identified at least in part by the sleep test.

In another embodiment, the present invention includes a method of diagnosing and treating sleep related airway obstructions of a subject comprising the steps of conducting a sleep test using a data acquisition system comprising at least one actuator and at least two sensors, the at least one actuator being an acoustic generator and the at least two sensors comprising an acoustic sensor and a body position sensor, the sleep test comprising the steps of measuring or estimating a subject's airway for obstruction(s) during sleep with the at least one actuator and the acoustic sensor and measuring or estimating the subject's body position during sleep with the at least one body position sensor of the data acquisition system, using the measured or estimated obstruction(s) and the measured or estimated body position determined during the sleep test, at least in part, to make a determination of tissue to be removed or extracted during surgery, and performing surgery to remove, at least in part, the obstruction(s) identified at least in part by the sleep test.

In still another embodiment, the present invention includes a method of diagnosing and treating sleep related airway obstructions of a subject comprising the steps of conducting a sleep test using a data acquisition system comprising at least one actuator and at least two sensors, the at least one actuator being an acoustic generator and the at least two sensors comprising an acoustic sensor and a sensor for measuring or estimating a subject's stage of sleep, the sleep test comprising the steps of measuring or estimating the subject's airway for obstruction(s) during sleep with the at least one actuator and the acoustic sensor and measuring or estimating the subject's stage of sleep with the at least one sleep stage sensor of the data acquisition system, using the measured or estimated obstruction(s) and the measured or estimated stage of sleep determined during the sleep test, at least in part, to make a determination of tissue to be removed or extracted during surgery, and performing surgery to remove, at least in part, the obstruction(s) identified at least in part by the sleep test.

In even another embodiment, the present invention includes a method of diagnosing and treating sleep related airway obstructions of a subject comprising the steps of conducting a sleep test using a data acquisition system comprising at least one actuator and at least one sensor, the at least one actuator being an acoustic generator and the at least one sensor being an acoustic sensor, the sleep test comprising the step of measuring or estimating a subject's airway for obstruction(s) during sleep with both the at least one actuator and at least one sensor of the data acquisition system, reviewing the sleep test to determine whether treatment is necessary or desired, conducting a second sleep test using the data acquisition system while titrating the subject with a PAP device to measure or estimate the effect of the PAP device on the subject's airway obstruction(s), and determining whether to continue having the subject use the PAP device or to perform surgery on the subject, based in part, on the measured or estimated effect of the PAP device on the subject's airway.

In even still another embodiment, the present invention includes a method of diagnosing and treating sleep related airway obstructions of a subject comprising the steps of conducting a sleep test using a data acquisition system comprising at least one actuator and at least two sensors, the at least one actuator being an acoustic generator and the at least two sensors comprising an acoustic sensor and a body position sensor, the sleep test comprising the steps of measuring or estimating a subject's airway for obstruction(s) during sleep with the at least one actuator and the acoustic sensor, and measuring or estimating the subject's body position during sleep with the at least one body position sensor of the data acquisition system, reviewing the sleep test to determine whether treatment is necessary or desired, conducting a second sleep test using the data acquisition system while titrating the subject with a PAP device to measure or estimate the effect of the PAP device on the subject's airway obstruction(s), and determining whether to continue having the subject use the PAP device or to perform surgery on the subject, based in part, on the measured or estimated effect of the PAP device on the subject's airway.

In still yet another embodiment, the present invention includes a method of diagnosing and treating sleep related airway obstructions of a subject comprising the steps of conducting a sleep test using a data acquisition system comprising at least one actuator and at least two sensors, the at least one actuator being an acoustic generator and the at least two sensors comprising an acoustic sensor and a sensor for measuring or estimating a subject's stage of sleep, the sleep test comprising the steps of measuring or estimating the subject's airway for obstruction(s) during sleep with the at least one actuator and the acoustic sensor and measuring or estimating the subject's stage of sleep with the at least one sleep stage sensor of the data acquisition system, reviewing the sleep test to determine whether treatment is necessary or desired, conducting a second sleep test using the data acquisition system while titrating the subject with a PAP device to measure or estimate the effect of the PAP device on the subject's airway obstruction(s), and determining whether to continue having the subject use the PAP device or to perform surgery on the subject, based in part, on the measured or estimated effect of the PAP device on the subject's airway.

In still yet another embodiment, the present invention includes a method of diagnosing sleep related airway obstructions of a subject comprising the steps of conducting a sleep test using a data acquisition system comprising at least one actuator and at least one sensor, the at least one actuator being an acoustic generator and the at least one sensor being an acoustic sensor, the sleep test comprising the step of measuring or estimating a subject's airway for obstruction(s) during sleep with both the at least one actuator and at least one sensor of the data acquisition system, and reviewing the sleep test to determine whether treatment is necessary or desired.

In still yet another embodiment, the present invention includes a method of diagnosing sleep related airway obstructions of a subject comprising the steps of conducting a sleep test using a data acquisition system comprising at least one actuator and at least two sensors, the at least one actuator being an acoustic generator and the at least two sensors comprising an acoustic sensor and a body position sensor, the sleep test comprising the steps of measuring or estimating a subject's airway for obstruction(s) during sleep with the at least one actuator and the acoustic sensor and measuring or estimating the subject's body position during sleep with the at least one body position sensor of the data acquisition system, and reviewing the sleep test to determine whether treatment is necessary or desired.

In still yet another embodiment, the present invention includes a method of diagnosing sleep related airway obstructions of a subject comprising the steps of conducting a sleep test using a data acquisition system comprising at least one actuator and at least two sensors, the at least one actuator being an acoustic generator and the at least two sensors comprising an acoustic sensor and a sensor for measuring or estimating a subject's stage of sleep, the sleep test comprising the steps of measuring or estimating the subject's airway for obstruction(s) during sleep with the at least one actuator and the acoustic sensor and measuring or estimating the subject's stage of sleep with the at least one sleep stage sensor of the data acquisition system, and reviewing the sleep test to determine whether treatment is necessary or desired.

In still yet another embodiment, the present invention includes a data acquisition device for sleep testing comprising at least one output channel, at least one input channel, and at least one electronic component, the at least one output channel transmitting signals and/or information to at least one acoustic generator, the at least one input channel for receiving electrical signals from at least one acoustic sensor, and the electronic component for digitizing, and storing or retransmitting a signal based on the received electrical signals.

In still yet another embodiment, the present invention includes a data acquisition device for sleep testing comprising at least one acoustic generator, at least one acoustic sensor, and at least three additional sensors, the acoustic generator used with the at least one acoustic sensor to measure or estimate an obstruction(s) in a subject's airway during sleep and the additional at least three sensors for determining at least the subject's respiratory effort/airflow, blood oxygen saturation, and heart rate during sleep.

In still yet another embodiment, the present invention includes a data acquisition device for sleep testing comprising at least one output channel and at least four input channels, the at least one output channel transmitting signals and/or information to at least one acoustic generator, the at least four input channels receiving electrical signals from at least one acoustic sensor and at least three physiological sensors for measuring other sleep parameters.

In still yet another embodiment, the present invention includes a data acquisition device for sleep testing comprising at least two output channels and at least one input channel, the at least two output channels transmitting signals and/or information to at least one acoustic generator and at least one positive airway pressure device, the at least one input channel receiving signals from at least one acoustic sensor.

In still yet another embodiment, the present invention includes a data acquisition device for sleep testing comprising at least two output channels and at least two input channels, the at least two output channels transmitting signals and/or information to at least one acoustic generator and at least one positive airway pressure device, the at least two input channels receiving signals from at least one acoustic sensor and at least one positive airway pressure device.

Additional features and advantages of the invention will be set forth in the detailed description that follows, and in part will be readily apparent to those skilled in the art from that description or recognized by practicing the invention as described herein, including the detailed description that follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, illustrate various embodiments of the invention and, together with the description, serve to explain the principles and operation of the invention.

BRIEF DESCRIPTION OF THE DRAWINGS

FIG. 9 a) Cross section of a micro electro-acoustic transducer used in various embodiments of the present invention, and b) a top view of the transducer in FIG. 9a.

FIG. 10 a) Cross section of another embodiment of another transducer being a micro piezoelectric acoustic transducer used in various embodiments of the present invention, and b) a top view of the transducer in FIG. 10a.

DESCRIPTION OF THE PREFERRED EMBODIMENTS

Figure 1:
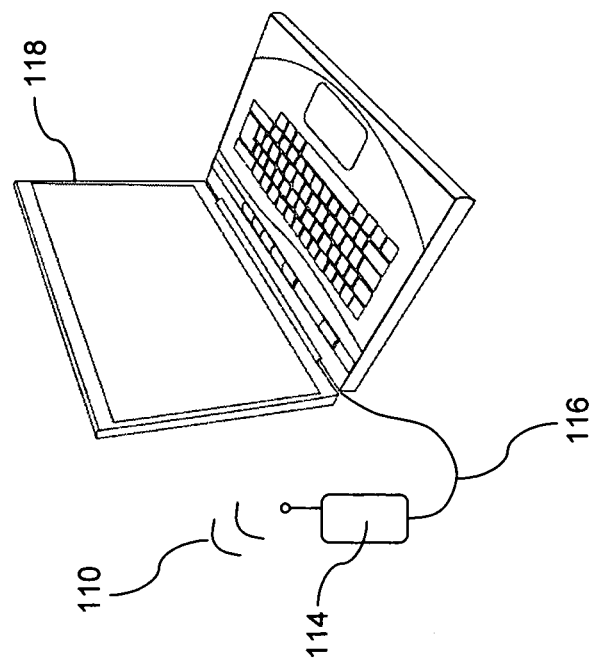
FIG. 1 Schematic diagram of one embodiment of the present invention used in a sleep diagnostic procedure.
Figure 1:
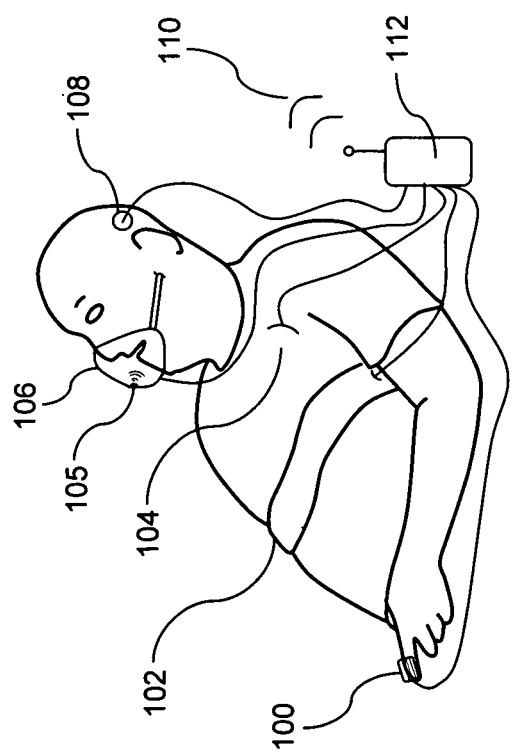

The present invention is related to a method of diagnosis and treatment of sleep disorders, and more particularly the use of an acoustic actuator and an acoustic sensor to determine airway obstructions and their locations as they relate to the subject's sleep stage, body position and sleep quality.

Various embodiments of the present invention use acoustic sensor(s) and/or acoustic generator(s) placed in or on a mask, cannula or mouthpiece in order to generate and/or measure various acoustic signals from a location proximal to a subject's airway. Acoustic information obtained using this approach is then used to determine airway obstructions and their locations as they relate to the subject's sleep state, body position and sleep quality.

Placement of the acoustic generator and acoustic sensor can vary depending upon application. For example, in some applications, the acoustic generator and/or acoustic sensor may be placed in the air hose of a positive airway pressure device. However, placement of the acoustic generator and/or acoustic sensor in this location may lead to significant attenuation of sound waves as they travel through the air hose if improperly placed. Because of this, positioning of these components preferably occurs at a location essentially proximal to a subject's airway. By essentially proximal to a subject's airway it is meant that the acoustic generator and/or acoustic sensor is placed either inside a subject's mouth or nose or within about 12 inches of the outside of the subject's mouth or nose, more preferably within about 8 inches of the outside of the subject's mouth or nose, even more preferably within about 4 inches of the outside of a subject's mouth or nose and most preferably within about 2 inches of the outside of a subject's mouth or nose. By positioning the acoustic generator and acoustic sensor essentially proximal to a subject's airway, attenuation of sound waves is minimized and ease of adaptation of acoustic variables to changing conditions, such as opening and closing of the mouth, is increased. Also by positioning the acoustic generator and sensor essentially proximal to a subject's airway it is easier and more effective to use higher frequency sounds, which serves to increase resolution of the location and characteristics of the obstruction.

In a preferred embodiment of the present invention, an acoustic sensor and an acoustic generator are placed in a mask used to acoustically monitor the state of a subject's airway during sleep diagnosis and therapy, particularly during sleep respiratory events. The acoustic sensor and generator can be any type known in the art including, but not limited to, electroacoustic and piezoelectric speakers and/or microphones. Optionally, in certain preferable embodiments of the present invention, a single acoustic transducer can be used as both an acoustic sensor and acoustic generator.

Acoustic monitoring of the state of a subject's airway is performed by application of sound waves to the subject's airway using the acoustic generator and subsequent measurement and observation of the behavior of these waves using the acoustic sensor. As acoustic waves travel down the airway, some of the waves are reflected as they contact various structures within the airway. These reflected waves are measured by the acoustic sensor, providing information about the state of a subject's airway and any obstructions which may be present in the subject's airway. Preferably, sound waves are applied to the subject's airway at a location proximal to the subject's nose or mouth and reflected sound waves are measured at a location proximal to the subject's nose or mouth. In its simplest application, acoustic data can provide a determination of whether a subject's airway is either open or closed. In other applications, the acoustic data can undergo more complex analysis to provide information on the degree and location of airway obstruction. In a still other applications, acoustic data can be used to calculate the cross-sectional area of the airway as a function of distance.

Various embodiments of the present invention use a data acquisition system capable of (a) receiving signals from sensors applied to or placed near a subject; (b) analyzing and comparing input signals from sensors applied to or placed near a subject (c) retransmitting the signals or transmitting another signal based at least in part on at least one of the collected signals; and (d) generating output signals for use by other devices optionally based in part on at least one of the collected signals. In its simplest form, the data acquisition system preferably should interface with sensors, retransmit signals from sensors, generate output signals for use by other devices and perform processing and analysis of signals received from sensors.

Various embodiments of the present invention use a data acquisition system capable of generating signals for use with an acoustic generator and recording signals from an acoustic sensor. Preferably, the data acquisition system is capable of emitting and recording a dynamic range of signals and the acoustic generator and acoustic sensor are capable of generating and sensing the same. It is envisioned that the range of signals capable of being generated and sensed by the device will extend from audible frequencies to ultrasonic frequencies, preferably, from about 20 Hz to about 20 MHz. More preferably, the acoustical waves are at ultrasonic frequencies. Due to the range of envisioned frequencies, various embodiments of the invention may use different models and/or types of acoustic generators and sensors in combination with several different types/versions of electronic hardware capable of producing and recording the desired frequencies. Preferably the acoustic generator and acoustic sensor are of small enough dimensions that they can be conveniently placed in a mask, mouthpiece, cannula or the like for use in or near a subject's mouth or nose.

In a preferred embodiment of the present invention, a standard time-of-flight calculation is performed by the data acquisition system to calculate the distance to a full or partial obstruction of a patient's airway. In a more preferred embodiment, a calculation of the difference between the emitted sound waves and reflected sound waves is used in combination with a standard time-of-flight calculation to provide information on both the distance to a full or partial obstruction and the nature and dynamic of the obstruction. In a still more preferred embodiment, the measurements above are performed during sleep, particularly, during sleepdisordered breathing events. The above illustrations are only examples of possible embodiments of the present invention and are not limitations.

Various embodiments of the present invention include the use of a data acquisition system capable of performing various methods or algorithms to analyze and correlate data and measurements from the various sensors used in the present invention in order to more effectively diagnose and/or treat obstructive respiratory sleep disorders. By way of example, but not limitation, the data acquisition system may correlate and/or coordinate signals from one or more of the afore and after-mentioned sensors and one or more external device(s) to develop the data or signals for use in, optionally, determining the quantitative level of severity of a subject's sleeping disorder and/or symptoms, determining the potential benefit(s) and/or effectiveness of PAP treatment for the subject, determining the potential benefit(s) and/or effectiveness of surgery in relieving the subject's symptoms and determining, at least in part, the location within the subject's airway where surgical removal or extraction of tissue would most likely prove successful in relieving the subject's symptoms.

If surgical removal or extraction of tissue from a subject's airway is performed, it can be accomplished using any of a number of methods, including, but not limited to, traditional surgical extraction, cauterization, and hot or cold surface ablation.

In one embodiment of the present invention, acoustic data collected using an acoustic generator and an acoustic sensor (hereinafter referred to as "acoustic data") pertaining to the state of a subject's airway is correlated with the subject's body position as measured by any of the methods set forth above. For example, when a subject changes position while sleeping, this change can be measured using cameras, accelerometers or the like. When a change in position is sensed, it can be communicated to the data acquisition system which can then initiate acoustic monitoring of the subject's airway in order to quantify any position-dependent change of the state of a subject's airway.

In another embodiment of the present invention, acoustic data pertaining to the state of a subject's airway is correlated by the data acquisition system with the subject's sleep stage. Sleep stage can be measured using a variety of methods and can be either roughly divided between stages or more finely divided, depending upon application. In one embodiment of the present invention, sleep stages are divided only between non-rapid eye movement (NREM) sleep and rapid eye movement (REM) sleep. The shift between REM and NREM sleep can be determined using relatively few sensors including, but not limited to, chin EMG and/or EOG sensors. This division between REM sleep and NREM sleep offers a useful approach to analysis and treatment of sleep disorders since significant physical and physiological changes occur between the two stages (e.g. sleep paralysis during REM sleep). In another embodiment of the present invention, further division of sleep stages can be performed using measurements of brain activity as observed with EEG. Using this approach, changes in EEG wave patterns combined with measurements from other sensors can be used to divide NREM sleep into four different stages (stages I-IV, respectively). In particular, changes in amplitude and frequency of EEG waves can be measured and used to determine which stage of NREM sleep a subject is in at any particular time.

Correlation of a subject's body position and/or sleep stage with acoustic data pertaining to the subject's airway state provides the physician, or other medical professional, with better information with which to make a diagnosis and, thus, presumably leads to better care for the subject. Specifically, correlation of a subject's body position and/or sleep stage with acoustic data pertaining to a subject's airway state provides greater insight into the nature of the subject's sleeping architecture as well as the nature and position of tissue in the subject's airway which could be contributing to, or causing, snoring, apneas or other obstructive respiratory disorders. Further, this information provides guidance to the physician or other medical professional in determining whether positive airway pressure (PAP) therapy may be beneficial in treating the subject's condition or whether a surgical approach may serve to more effectively provide relief to the subject.

Various embodiments of the present invention include the use of a data acquisition system capable of exchanging data with a PAP device, and the use of a PAP device capable of exchanging data with the data acquisition system. In one embodiment, the data acquisition system is used to coordinate the step of acoustic monitoring of a subject's airway with changes in pressure output of the PAP device. In this embodiment, the data acquisition system, upon receiving data from the PAP device indicating that the PAP has undergone a change in output pressure, will initiate acoustic monitoring of a subject's airway. This allows correlation of PAP pressure with airway state, which provides a method of examining the potential effectiveness of PAP treatment as well as greater resolution of the location of obstructive tissue within the subject's airway. In another embodiment of the present invention, PAP pressure is correlated with acoustic data pertaining to a subject's airway state in order to localize obstructive tissue within the subject's airway. In this embodiment, PAP pressure is increased and decreased through a number of cycles in combination with acoustic monitoring in order to refine and increase the resolution of acoustic localization of the obstructive tissue. Still other embodiments involve various combinations of those embodiments described above, including cycling of PAP pressure to refine obstruction location and examine PAP treatment effectiveness during a single procedure. It is envisioned that information obtained using this embodiment would be used to guide and plan surgical intervention on behalf of a subject although this information would clearly also be useful in other applications including determination of effectiveness of, and approach to, PAP treatment.

In still another embodiment of the present invention, acoustic data pertaining to a subject's airway state is correlated by the data acquisition system with sleep respiratory events as measured by other sensors, such as snore and respiratory sensors. In this embodiment, sensing of a respiratory event by other sensors of the system would trigger the data acquisition system to initiate acoustic monitoring of the subject's airway in order to provide acoustic information pertaining to the cause of the respiratory event.

The various embodiments described above are given as examples only and are not intended to limit the present invention. Other embodiments of the present invention use various combinations of those embodiments described above. For example, in a preferable embodiment of the present invention, acoustic data, body position, sleep stage, respiratory events, and input from other sensors (e.g. respiratory sensors) are simultaneously correlated by the data acquisition system during a sleep test in order to provide multivariable examination of the nature of a subject's sleep disorder as well as the location of obstructive tissue within the subject's airway in the case of obstructive sleep disorders. In another example, acoustic data, body position, sleep stage, respiratory events, input from other sensors (e.g. respiratory sensors) and PAP pressure measurements are simultaneously correlated by the data acquisition system during a PAP titration procedure in order to provide increased understanding of the nature of a subject's sleep disorder, potential effectiveness of PAP treatment for the subject, and information on the location of obstructive tissue that may be surgically removed in order to provide relief to the subject. Such an approach not only allows insight into potential PAP effectiveness, but also provides insight into the viability and potential success of surgical intervention, thus providing valuable pre-surgical planning information.

For various embodiments described above, results of correlation of the various sensors performed by the data acquisition system of the present invention are preferably output to a visual display for review, examination, modification and/or adjustment by a physician or other trained medical professional such as a sleep technologist. Using this information, the physician or other medical professional then makes a diagnosis and chooses a desired course of treatment or orders further testing. The results of the correlation of the various sensors can also be used in a closed or partially closed loop control system to titrate the subject's treatment.

The data acquisition system used with the present invention can, optionally, be comprised of a single box, such as a patient interface box, containing a sensor interface module, a pre-processor module, a transmitter module and an output module. Further optionally, the data acquisition system could consist of several boxes that communicate with each other, each box containing one or more modules. For example, the data acquisition system could consist of: (a) a patient interface box containing a sensor interface module, a pre-processor, a transmitter, a receiver and an output module; and (b) a base station box containing a second pre-processor, a transmitter, and a receiver. In this example, the transmitter and receiver of the patient interface box are used to communicate with the base station box. The transmitter and receiver of the base station box are used to both communicate with the patient interface box and a remote monitoring station, remote analysis station, remote data storage station, or the like. Similarly, the data acquisition system could consist of (a) a patient interface box containing a sensor interface module, a transmitter, a receiver and an output module; (b) a processor box containing a pre-processor, a transmitter, and a receiver; and (c) a base station box containing only a receiver and a transmitter. Further optionally, the data acquisition system could consist of (a) a patient interface box containing a sensor interface module, a pre-processor, a transmitter, a receiver and an output module; (b) a base station box containing a pre-processor, a transmitter, a receiver and an output module; and (c) an external data processing and storage device containing at least a processor, a transmitter, a receiver and an output module. In this example, the transmitter and receiver of the patient interface box are used to communicate with the base station box. The transmitter, receiver and output module of the base station box are used to both communicate with, and receive communication from, the patient interface box and an external data processing and storage device such as a notebook computer. This allows more complex data processing to take place within an external data processing device while the results of such processing can be communicated via the base station to the patient interface device to modulate recording and output of the patient interface device. In these configurations, it is not necessary for the transmitters to be of the same type. For example, the transmitter in the patient interface box can be a wired, Bluetooth, or other transmitter designed for short distances, and the transmitter in the base station box can be a WiFi, IEEE 802.11, TCP/IP, or other transmitter designed to establish connections over larger distances.

The data acquisition system of the present invention is preferably portable. By portable, it is meant, among other things, that the device is capable of being transported relatively easily. Relative ease in transport means that the device is easily worn and carried, generally in a carrying case, to the point of use or application and then worn by the subject without significantly affecting any range of motion. Furthermore, any components of the data acquisition system that are attached to or worn by the subject, such as the sensors and patient interface box, should also be lightweight. Preferably, these subject-contacting components of the device (including the sensors and the patient interface box) weigh less than about 10 lbs., more preferably less than about 7.5 lbs., even more preferably less than about 5 lbs., and most preferably less than about 2.5 lbs. The subject-contacting components of the device preferably are battery-powered and use a data storage memory card and/or wireless transmission of data, allowing the subject to be untethered. Furthermore, the entire data acquisition system (including the subject-contacting components as well as any other sensors, a base station, or other components) preferably should be relatively lightweight. By relatively lightweight, it is meant preferably the entire data acquisition system, including all components such as any processors, computers, video screens, cameras, and the like preferably weigh less in total than about 20 lbs., more preferably less than about 15 lbs., and most preferably less than about 10 lbs. This data acquisition system preferably can fit in a reasonably sized carrying case so the subject or assistant can easily transport the system. By being lightweight and compact, the device should achieve greater acceptance for use by the subject.

Various embodiments of the present invention use a data acquisition system capable of storing and/or retransmitting the signals from the sensors or storing and/or transmitting another signal based at least in part on at least one of the sensor signals. The data acquisition system can be programmed to send all signal data to the removable memory, to transmit all data, or to both transmit all data and send a copy of the data to the removable memory. When the data acquisition system is programmed to store a signal or pre-processed signal, the signals from the sensors can be saved on a medium in order to be retrieved and analyzed at a later date. Media on which data can be saved include, but are not limited to chart recorders, hard drive, floppy disks, computer networks, optical storage, solid-state memory, magnetic tape, punch cards, etc. Preferably, data are stored on removable memory. For both storing and transmitting or retransmitting data, flexible use of removable memory can either buffer signal data or store the data for later transmission. Preferably, nonvolatile removable memory can be used to customize the system's buffering capacity and completely store the data.

If the data acquisition system is configured to transmit the data, the removable memory acts as a buffer. In this situation, if the data acquisition system loses its connection with the receiving station, the data acquisition system will temporarily store the data in the removable memory until the connection is restored and data transmission can resume. If, however, the data acquisition system is configured to send all data to the removable memory for storage, then the system does not transmit any information at that time. In this situation, the data stored on the removable memory can be retrieved by either transmission from the data acquisition system, or by removing the memory for direct reading.

The method of directly reading the memory will depend on the format of the removable memory. Preferably the removable memory is easily removable and can be removed instantly or almost instantly without tools. The memory is preferably in the form of a card and most preferably in the form of a small easily removable card with an imprint (or upper or lower surface) area of less than about two square inches. If the removable memory is being used for data storage, preferably it can write data as fast as it is produced by the system, and it possesses enough memory capacity for the duration of the test. These demands will depend on the type of test being conducted, tests requiring more sensors, higher sampling rates, and longer duration of testing will require faster write speeds and larger data capacity. The type of removable memory used can be almost any type that meets the needs of the test being applied. Some examples of the possible types of removable memory that could be used include but are not limited to Flash Memory such as CompactFlash, SmartMedia, Miniature Card, SD/MMC, Memory Stick, or xD-Picture Card. Alternatively, a portable hard drive, CD-RW burner, DVD-RW burner or other data storage peripheral could be used. Preferably, a SD/MMC-flash memory card is used due to its small size. A PCMCIA card is least preferable because of the size and weight.

When the data acquisition system is programmed to retransmit the signals from the sensors, preferably the data acquisition system transmits the signals to a processor for analysis. More preferably, the data acquisition system immediately retransmits the signals to a processor for analysis. Optionally, the data acquisition system receives the signals from one or more of the aforementioned sensors and stores the signals for later transmission and analysis. Further optionally, the data acquisition system both stores the signals and immediately retransmits the signals.

When the data acquisition system is programmed to retransmit the signals from the sensors or transmit a signal based at least in part on the signal from the sensors (collectively "to transmit" in this section), the data acquisition system can transmit through either a wireless system, a tethered system, or some combination thereof. When the system is configured to transmit data, preferably the data transmission step utilizes a two-way (bi-directional) data transmission. Using two-way data transmission significantly increases data integrity. By transmitting redundant information, the receiver (the processor, monitoring station, or the like) can recognize errors and request a renewed transmission of the data. In the presence of excessive transmission problems, such as transmission over excessive distances or obstacles absorbing the signals, the data acquisition system can control the data transmission or independently manipulate the data. With control of data transmission it is also possible to control or re-set the parameters of the system, e.g., changing the transmission channel or encryption scheme. For example, if the signal transmitted is superimposed by other sources of interference, the receiving component could secure a flawless transmission by changing the channel. Another example would be if the transmitted signal is too weak, the receiving component could transmit a command to increase the transmitting power. Still another example would be for the receiving component to change the data format of the transmission, e.g., in order to increase the redundant information in the data flow. Increased redundancy allows easier detection and correction of transmission errors. In this way, safe data transmissions are possible even with the poorest transmission qualities. This technique opens a simple way to reduce the transmission power requirements, thereby reducing the energy requirements and providing longer battery life. Another advantage of a bi-directional digital data transmission lies in the possibility of transmitting test codes in order to filter out external interferences, for example, refraction or scatter from the transmission current. In this way, it is possible to reconstruct falsely transmitted data.

Data compression using lossless encoding techniques can provide basic throughput optimization, while certain lossy encoding techniques will offer far greater throughput while still providing useful data. Lossy encoding techniques may include but are not limited to decimation, or transmission of a compressed image of the data. The preferred method for encoding will include special processing from the transmitter that will preprocess the data according to user-selectable options, such as digital filtering, and take into the account the desired visual representation of that information, such as pixel height and target image width. Facilities can be made within the system to control the encoding in order to optimize utilization on any given network. Control over the encoding methods may include, but is not limited to selection of a subset of the entire set of signals, target image size, and decimation ratio.

Data encryption can be applied to secure data transmissions over any network. Encryption methods may include but are not limited to simple obfuscation and sophisticated ciphers. The preferred embodiment of secure data transmission that is compatible with HIPAA and HCFA guidelines will be implemented using a virtual private network. More preferably, the virtual private network will be implemented using a specialized security appliance, such as the PIX 506E, from Cisco Systems, Inc, capable of implementing IKE and IPSec VPN standards using data encryption techniques such as 168-bit 3DES, 256-bit AES, and the like. Still more preferably, secure transmission will be provided by a third party service provider or by the healthcare facility's information technology department. The system will offer configuration management facilities to allow it to adapt to changing guidelines for protecting patient health information (PHI).

Several preferable embodiments of the invention employ a wireless data acquisition system. This wireless data acquisition system consists of several components, each wirelessly connected. Data is collected from the sensors described above by a patient interface box. The patient interface box then wirelessly transmits the data to a separate signal pre-processing module, which then wirelessly transmits the pre-processed signal to a receiver. Alternatively, the patient interface box processes the signal and then directly transmits the processed signal to the receiver using wireless technology. Further alternatively, the patient interface box wirelessly transmits the signals to the receiver, which then pre-processes the signal. Preferably, the wireless technology used by the data acquisition system components is radio frequency based. Most preferably, the wireless technology is digital radio frequency based. The signals from the sensors and/or the pre-processed signals are transmitted wirelessly to a receiver, which can be a base station, a transceiver hooked to a computer, a personal digital assistant (PDA), a cellular phone, a wireless network, or the like. Most preferably, the physiological signals are transmitted wirelessly in digital format to a receiver.

When a component of the wireless data acquisition system is configured to wirelessly transmit data, it is preferably capable of conducting a radio frequency sweep to detect an occupied frequency or possible interference. The system is capable of operating in either "manual" or "automatic" mode. In the manual mode, the system conducts an RF sweep and displays the results of the scan to the system monitor. The user of the system can then manually choose which frequency or channel to use for data transmission. In automatic mode, the system conducts a RF sweep and automatically chooses which frequencies to use for data transmission. The system also preferably employs a form of frequency hopping to avoid interference and improve security. The system scans the RF environment then picks a channel over which to transmit based on the amount of interference occurring in the frequency range.

In the present invention, transmitting the data wirelessly means that the data is transmitted wirelessly at least in part of the data transfer process. This means, for example, that the data may be transmitted wirelessly from the patient interface box to the base station, which then transmits the data via either a wireless method, such as a wireless cellular card, local wireless network, satellite communication system, and the like, or a wired method, such as a wired internet connection, the testing facility's LAN, and the like. Transmitting the data wirelessly also means, for example, that the data may be transmitted via wired connection from the patient interface box to a base station, which then wirelessly transmits the data via any wireless method, such as Bluetooth, IEEE 802.11, wireless cellular card, satellite communication system, and the like to a database that distributes the data over a hardwired system to a sleep unit or lab. Transmitting the data wirelessly also means, for example, that the data may be wirelessly transmitted directly from the patient interface box via WiFi or IEEE 802.11, Bluetooth, wireless cellular card, and the like to a processor, which then transmits the processed data to the sleep unit or laboratory. Preferably, the patient interface box wirelessly transmits the data. This allows for a simplified subject hookup and improved subject mobility.

Preferably, the data acquisition system retransmits the signals from the sensors applied to the subject or transmits a signal based at least in part on at least one of the physiological, kinetic, acoustic or environmental signals at substantially the same time as the signal is received or generated. At substantially the same time preferably means within approximately one hour. More preferably, at substantially the same time means within thirty minutes. Still preferably, at substantially the same time means within ten minutes. Still more preferably, at substantially the same time means within approximately one minute. Still more preferably, at substantially the same time means within milliseconds of when the signal is received or generated. Most preferably, a substantially same time means that the signal is transmitted or retransmitted at a nearly instantaneous time as it is received or generated. Transmitting or retransmitting the signal at substantially the same time allows the physician or other trained medical professional to review the acoustic, physiological, kinetic and environmental signals and if necessary to make a determination, which could include modifying the subject's treatment protocols or instructing the subject to adjust the sensors.

The receiver (base station, remote communication station, or the like) of various embodiments of the wireless data acquisition system can be any device known to receive RF transmissions used by those skilled in the art to receive transmissions of data. By way of example but not limitation, the receiver can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the receiver can further transmit data to another device and/or back. Further optionally, two different receivers can be used, one for receiving transmitted data and another for sending data. For example, with the wireless data acquisition system used in the present invention, the receiver can be a wireless router that establishes a broadband internet connection and transmits the physiological signal to a remote Internet site for analysis, preferably by the subject's physician or another clinician. Other examples of a receiver are a PDA, computer, or cell phone that receives the data transmission, optionally re-processes the information, and re-transmits the information via cell towers, land phone lines, or cable to a remote processor or remote monitoring site for analysis. Other examples of a receiver are a computer or processor that receives the data transmission and displays the data or records it on some recording medium that can be displayed or transferred for analysis at a later time. Optionally, two or more receivers can be used simultaneously. For example, the patient interface box can transmit signals to a base station receiver that processes and retransmits the signals, as well as a PDA receiver that displays the signals for a clinician to review.

Various embodiments of the present invention include various steps. These steps are examples of the steps that are optionally used in this invention. One step is determining whether the subject being analyzed for a sleep disorder maintained a normal sleeping pattern prior to beginning appropriate sleep diagnostic procedures and treatment. This step can be performed or accomplished in a number of ways. In the simplest form, the subject can be questioned regarding his or her previous sleep patterns. In a somewhat more complex form the subject can be requested to fill out a questionnaire, which then can be graded to determine whether his or her previous sleep patterns were normal (or appeared normal). In still another form, this step may include a physician or other medically trained individual determining whether a subject snores or sleeps irregularly through examination of physical or physiological indicators associated with certain sleep disorders. One of the objectives of this step is to ensure that the results of the subject's sleep analysis test are not the result of or affected by the subject's previous lifestyle or environmental factors (i.e., intentional lack of sleep, etc). It is clear that there are numerous ways beyond those examples mentioned of determining whether the subject being analyzed maintained or thought they were maintaining a normal sleeping pattern prior to analysis. Therefore, the examples given above are included as exemplary rather than as limiting, and those ways of determining whether the subject maintained or thought they were maintaining a normal sleeping pattern known to those skilled in the art are considered to be included in the present invention.

Another step may be determining whether a subject suffers from, or is likely to suffer from, a sleep disorder. This determination can be performed or accomplished in a number of ways including, but not limited to, the use of various forms of sleep testing as described above. Sleep testing is a method of examining a subject's sleep health using sensors to acquire physical and/or physiological measurements from a subject during sleep. In its simplest form, sleep testing can consist of the use of a single sensor to monitor a subject's sleep quality. In more complex forms, more sensors may be used such as is common in polysomnography.

Still another step may include applying at least one sensor to a subject. The sensors can be applied at any location.

Preferably, the sensors are applied in a physician's office or place of business. The physician's place of business includes but is not limited to an office building, a freestanding sleep center, location within a hospital, mobile vehicle or trailer, leased space, or similar location. Just as preferably, the sensors could be mailed to the subject's home or other sleeping location, and the subject will then apply them independently. The subject's sleeping location includes but is not limited to the subject's home, apartment, and the like, as well as a hotel, nursing facility, or other location where an individual could sleep and where this analysis could be done more controllably and/or less expensively than in a sleep laboratory or hospital setting.

The sensors that are used with various embodiments of the present invention are described herein but can also be any of those known to those skilled in the art for the applications of this method. The sensors may be traditional and non-traditional sensors related to the subject's quality of sleep. These sensors may collect physiological, kinetic, and environmental signals. Preferably, those sensors include, but are not limited, to wet or dry electrodes, photodetectors, accelerometers, pneumotachometers, sphygmomanometers, strain gauges, thermal sensors, pH sensors, chemical sensors, gas sensors (such as oxygen and carbon dioxide sensors), transducers, piezo sensors, magnetometers, pressure sensors, static charge-sensitive beds, microphones, audio recorders, audio transducers, video cameras, and the like. The invention is envisioned to include those sensors subsequently developed by those skilled in the art to detect these types of signals. For example, the sensors can be magnetic sensors. Because electro-physiological signals are, in general, electrical currents that produce associated magnetic fields, the present invention further anticipates methods of sensing those magnetic fields to acquire the signal. For example, new magnetic sensors could collect brain wave signals similar to those that can be obtained through a traditional electrode applied to the subject's scalp.

Various embodiments of the present invention include a step for applying sensors to the subject. This step can be performed or accomplished in a number of ways. In the simplest form, one sensor is applied to the subject to measure a single channel of physiological or kinetic data. Preferably; the set of sensors used includes at least one pulse oximeter, one thoracic respiratory effort belt applied around the subject's chest, at least one sensor for measuring heart rate and one acoustic sensor situated in or near the subject's mouth. In a still more complex form of this step, multiple sensors are applied to the subject to collect data sufficient for a full PSG test. If PSG data are to be collected, the preferred minimal set of sensors for the present invention includes sensors for two electroencephalography (EEG) channels, one electroocculography (EOG) channel, one chin electromyography (EMG) channel, one airflow channel, one electrocardiography (ECG) channel, one thoracic respiratory effort channel, one abdominal respiratory effort channel, one pulse oximetry channel, one shin or leg EMG channel, and at least one channel for input from an acoustic sensor. In another preferable embodiment, the minimal set of PSG sensors is augmented with at least one additional channel of EOG, one channel of snore, one channel of body position (ex., an accelerometer), one channel of video, and optionally one channel of audio.

Electro-physiological signals such as EEG, ECG, EMG, EOG, electroneurogram (ENG), electroretinogram (ERG), and the like can be collected via electrodes placed at one or several relevant locations on the subject's body. For example when measuring brain wave or EEG signals, electrodes may be placed at one or several locations on the subject's scalp. In order to obtain a good electro-physiological signal, it is desirable to have low impedances for the electrodes. Typical electrodes placed on the skin may have an impedance in the range of from 5 to 10 kΩ. It is in generally desirable to reduce such impedance levels to below 2 kΩ. A conductive paste or gel may be applied to the electrode to create a connection with an impedance below 2 kΩ. Alternatively or in conjunction with the conductive gel, a subject's skin may be mechanically abraded, the electrode may be amplified, or a dry electrode may be used. Dry physiological recording electrodes of the type described in U.S. Pat. No. 7,032,301 are herein incorporated by reference. Dry electrodes are advantageous because they use no gel that can dry out, skin abrasion or cleaning is unnecessary, and the electrode can be applied in a hairy area such as the scalp. Additionally if electrodes are used as the sensors, preferably at least two electrodes are used for each channel of data—one signal electrode and one reference electrode. Optionally, a single reference electrode may be used for more than one channel.

Other sensors can be used to measure various parameters of a subject's respiration. Measurement of airflow is preferably performed using sensors or devices such as a pneumotachometer, strain gauges, thermal sensors, transducers, piezo sensors, magnetometers, pressure sensors, static charge-sensitive beds, and the like. These sensors or devices also preferably measure nasal pressure, respiratory inductance plethysmography, thoracic impedance, expired carbon dioxide, tracheal sound, snore sound, blood pressure and the like. Measurement of respiratory effort is preferably measured by a respiration piezoelectric sensor, inductive plethysmography esophageal pressure, surface diaphragmatic EMG, and the like. Measurement of oxygenation and ventilation is preferably measured by pulse oximetry, transcutaneous oxygen monitoring, transcutaneous carbon dioxide monitoring, expired end carbon dioxide monitoring, and the like.

One example of such a sensor for measuring respiration either directly or indirectly is a respiration belt. Respiration belts can be used to measure a subject's abdominal and/or thoracic expansion over a measurement time period. The respiration belts may contain a strain gauge, piezo-electric, pressure transducer, or other sensors that can indirectly measure a subject's respirations and the variability of respirations by providing a signal that correlates to the thoracic/abdominal expansion/contractions of the subject's thoracic/abdominal cavity. If respiration belts are used, they may be placed at one or several locations on the subject's torso or in any other manner known to those skilled in the art. Preferably, when a thoracic respiration belt is used, it is positioned below the axilla to measure rib cage excursions. When an abdominal respiration belt is used, it is positioned at the level of the umbilicus to measure abdominal excursions. Optionally, at least two belts are used, with one positioned at the axilla and the other at the umbilicus.

Another example of a sensor or method for measuring respiration either directly or indirectly is a nasal cannula or a facemask used to measure the subject's respiratory airflow. Nasal or oral airflow can be measured quantitatively and directly with a pneumotachograph consisting of a pressure transducer connected to either a standard oxygen nasal cannula placed in the nose, a facemask over the subject's mouth and nose, or a PAP or CPAP gas delivery mechanism. Airflow can be estimated by measuring nasal or oral airway pressure that decreases during inspiration and increases during expiration. Inspiration and expiration produce fluctuations on the pressure transducer's signal that are proportional to airflow. A single pressure transducer can be used to measure the combined oral and nasal airflow. Alternatively, the oral and nasal components of these measurements can be acquired directly through the use of at least two pressure transducers, one transducer for each component. Optionally, the pressure transducer(s) are internal to the patient interface box. If two transducers are used for nasal and oral measurements, preferably each has a separate air port into the patient interface box.

Still another example of a sensor or method of directly or indirectly measuring a subject's respiration is the pulse oximeter. The pulse oximeter can measure the oxygenation of the subject's blood by producing a source of light at two wavelengths (typically at 650 nm and 905, 910, or 940 nm). Hemoglobin partially absorbs the light by amounts that differ depending on whether it is saturated or desaturated with oxygen. Calculating the absorption at the two wavelengths leads to an estimate of the proportion of oxygenated hemoglobin. Preferably, pulse oximeters are placed on a subject's earlobe or fingertip. More preferably, the pulse oximeter is placed on the subject's index finger. In one embodiment of the present invention, a pulse oximeter is built-in or hard-wired to a data acquisition system. Alternatively, the pulse oximeter can be a separate unit in communication with a data acquisition system via either a wired or a wireless connection.

Other sensors can be used to measure various parameters associated with the subject's movement, posture and body position during sleep. For example, kinetic data can be obtained by accelerometers or gyroscopes placed on the subject. In one embodiment, several accelerometers can be placed in various locations on the subject, for example on the wrists, torso, and legs. These accelerometers can provide both motion, posture and body position data by measuring gravity. These accelerometers can be used to detect when a subject goes to sleep and/or to detect movements and posture during sleep which are important factors in assessing the subject's actual sleep time which is an important parameter used to generate an accurate assessment of sleep quality and sleep respiratory events. A video signal can also be used to provide data on a subject's posture and body position during sleep. Alternatively, stereo video signals can provide three-dimensional body position and motion information. If a video signal is used to measure posture, movement or body position, preferably, the video signal is acquired using a digital camera. More preferably, the camera is a wireless digital camera. Still more preferably, the camera is a wireless digital infrared camera. In one specific embodiment of the present invention, video may be used with specially marked electrodes or other suitable high-contrast markers. The electrodes can be any appropriate electrode known in the art. The only change to the electrode is that they preferably have predetermined high contrast marks on them to make them easily visible to the video camera. These markings enable the video system to accurately distinguish the electrodes from the rest of the video image. Using the markings on each electrode, the system can then calculate the movement and/or body position of a subject. In still another embodiment of the invention, the system can detect subject movement by monitoring the actual movement of the subject's body without the use of high-contrast markers or electrodes.

Kinetic data collected by the various aforementioned sensors also includes but is not limited to frequent tossing and turning indicative of an unsuitable mattress, excessive movement of bedding indicating unsuitable sleeping temperatures and unusual movement patterns indicating pain. Additionally, alternative analysis of the video signal can be used in diagnosis of certain sleeping disorders, such as restless legs syndrome (RLS), sleepwalking, or other parasomnia.

Other sensors can be used to measure various parameters of a subject's sleeping environment. Environmental parameters can be measured by video cameras, microphones (to detect noise level, etc.), photodetectors, light meters, thermal sensors, particle detectors, chemical sensors, mold sensors, olfactory sensors, barometers, hygrometers, and the like. Measurement of environmental data can provide insight into the subject's sleeping location and habits that is unavailable in the traditional laboratory setting. Environmental data can indicate that the subject's sleeping location is a potential source of the subject's sleeping difficulty. By way of example, but not limitation, environmental data can indicate that the subject's sleeping location has an unsuitable temperature, humidity, light level, noise level, or air quality. For example, these environmental conditions can cause sweating, shivering, sneezing, coughing, noise, and/or motion that disrupts the patient's sleep. The environmental sensors can be placed anywhere in the subject's sleeping location or on the subject, if appropriate. Preferably, the environmental sensors are placed near, but not necessarily on, the subject.

Sensors placed in/on a mask, cannula or mouthpiece can also be used to determine other physiological characteristics. For example, software filtering can obtain "snore signals" from a single pressure transducer signal by extracting the high frequency portion of the transducer signal. This method can eliminate the need for a separate sensor, such as a microphone or another transducer and also reduces the system resources required to detect both snore and airflow. In another example, a modified nasal cannula or facemask connected to a carbon dioxide or, oxygen sensor may be used to measure respective concentrations of these gases. In still another example, various acoustic sensors and/or acoustic generators for use with acoustic sensors can be placed in a mask, cannula or mouthpiece in order to generate and/or measure various acoustic signals from a location proximal to a subject's mouth, as described above.

Various embodiments of the present invention include the step of connecting sensors to a data acquisition system. The sensors can be connected to the data acquisition system either before or after they are applied to the subject. The sensors can be permanently hardwired to at least part of the data acquisition system. More preferably, the sensors are connected to at least part of the data acquisition system via a releasable connector. Optionally, the sensors can be connected to at least part of the data acquisition system via non-releasable connector that does not permit disconnection without destruction of the connector. The physiological sensors are generally hardwired (permanently or via a connector) to the data acquisition system, but the ongoing evolution in wireless sensor technology may allow sensors to contain transmitters. Optionally, such sensors are wirelessly connected to the data acquisition system. As such, these sensors and the wireless connection method are considered to be part of the present invention. With the advances in microelectromechanical systems (MEMS) sensor technology, the sensors may have integrated analog amplification, integrated A/D converters, and integrated memory cells for calibration, allowing for some signal conditioning directly on the sensor before transmission.

Preferably, the sensors are all connected in the same way at the same time, although this certainly is not required. It is possible, but less preferable, to connect the sensors with a combination of methods (i.e., wired or wireless) at a combination of times (i.e., some before application to the subject, and some after application to the subject). The sensors can be connected to various parts of the data acquisition system. For example, a thoracic respiratory effort belt can be connected to a patient interface box while a pulse oximeter can be connected a base station. Further, some sensors may not be attached to the subject at all. Examples of such sensors include video cameras or microphones that are placed in the subject's sleeping area. Although these sensors are not attached to the subject, they are still connected to at least one component of the data acquisition system using any of the methods of sensor connection mentioned above.

Turning now to a description of the figures, FIG. 1 shows a schematic diagram of a subject using one embodiment of the present invention. In FIG. 1, a data acquisition device 112 receives signals from various sensors placed on the subject 100, 102, 104, 105, 106, 108. These sensors may for example be blood oxygen saturation sensors 100, respiratory sensors 102, ECG sensors 104, acoustic transducers to sense sound 105, EEG sensors 108, or any of the other sensors described herein or known in the art. Although only five types of sensors are shown, the data acquisition device is capable of accepting input signals from multiple additional sensors or using as few as few as one sensor. Also shown in FIG. 1 is a mask 106 used to support and position the acoustic transducer 105. The acoustic transducer 105 is capable of both generating and recording sound waves. Although the mask 106 shown here is a face mask, covering both the nose and mouth of the subject, in other embodiments the mask used can be an oral mask, covering only the mouth, or a nasal mask or nasal cannula, covering or entering only through the nose. In still other embodiments, a mouthpiece could be used to support and position the acoustic transducer 105, eliminating the need for use of a mask. The data acquisition device 112 can produce signals used to modulate output of the acoustic transducer 105, store the data received from the various sensors, transmit the data to a remote location, and/or both transmit and store data received from the sensors. In the present case, data is transmitted via wireless signal 110 to a base station 114 which receives the signal 110 and transfers the data to an external programming and analysis device 118, shown here as a notebook computer, via a data interface cable 116. The external programming and analysis device 118 can then further transmit sleep data to a remote location using the internet or other communication means (not shown) and/or perform analysis of data and communicate desired results back to the data acquisition device for use in modulation of data acquisition device input or output settings.

Figure 2:
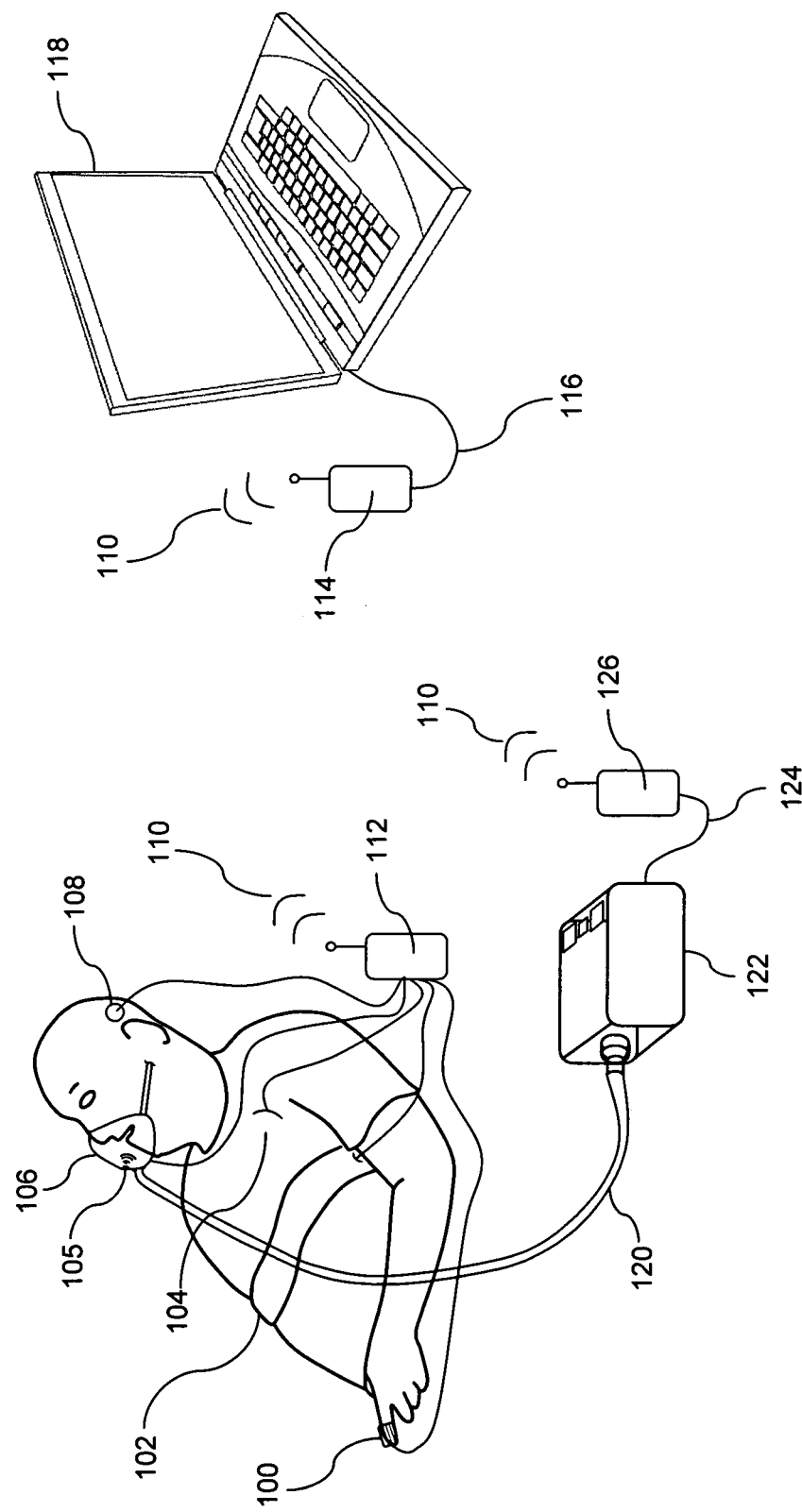
FIG. 2 Schematic diagram of one embodiment using acoustic location to titrate the subject use of a positive airway pressure device.

Turning now FIG. 2 a schematic diagram of a subject using another embodiment of the present invention is shown. In FIG. 2, a data acquisition device 112 receives signals from various sensors placed on the subject 100, 102, 104, 106, 108. These sensors can be blood oxygen saturation sensors 100, respiratory sensors 102, ECG sensors 104, acoustic transducers to sense sound 105, EEG sensors 108, or any of the other sensors described herein or known in the art. Although only five types of sensors are shown, the data acquisition device is capable of accepting input signals from multiple additional sensors or using as few as one sensor. Also shown in FIG. 2 is a mask 106 used to support and position the acoustic transducer 105. The acoustic transducer 105 is capable of both generating and recording sound waves. Although the mask 106 shown here is a face mask, covering both the nose and mouth of the subject, in other embodiments the mask used can be an oral mask, covering only the mouth, or a nasal mask or nasal cannula, covering or entering only the nose. In still other embodiments, a mouthpiece could be used to support and position the acoustic sensor 105, eliminating the need for use of a mask.

In this embodiment, the mask 106 provides means for attachment of the mask to a positive airway pressure device 122 ("PAP device") using an air hose 120. The positive airway pressure device 122 supplies positive pressure to the subject's airways using the mask 106 and the air hose 120 allowing analysis and treatment of the subject's sleep disorder. Here, the positive airway pressure device 122 is connected via a data interface cable 124 to a treatment interface device 126. The treatment interface device 126 is capable of communicating with the positive airway pressure device as well as with various components of the data acquisition system of the present invention including the data acquisition device 112 and the base station 114. Preferably, communication between the treatment interface device 126 and the various components of the data acquisition system occurs wirelessly 110. A shown here, acoustic and physiologic data recorded by the data acquisition device 112 from the acoustic transducer 105 and other sensors is analyzed by either the data acquisition device 112 or the external programming and analysis device 118. This data can then be used to adjust the pressure output of the positive airway pressure device 122 by communicating the desired pressure to the treatment interface device 126. Alternatively, instead of PAP device 122 output pressure being modulated by input from the data acquisition system, PAP device 122 output pressure may be manually adjusted by a physician or other medical professional and this change communicated to the data acquisition device 112 or base station 114 where it can be used for sleep data analysis and/or modulation of data acquisition system input or output settings.

The data acquisition device 112 can produce signals used to modulate output of the acoustic transducer 105, store the data received from the various sensors, transmit the data to a remote location, and/or both transmit and store data received from the sensors. In the present case, data is transmitted via wireless signal 110 to a base station 114 which receives the signal 110 and transfers the data to an external programming and analysis device 118, shown here as a notebook computer, via a data interface cable 116. The external programming and analysis device 118 can then further transmit sleep data to a remote location using the internet or other communication means (not shown) and/or perform analysis of data and communicate desired results back to the data acquisition device for use in modulation of data acquisition device input or output settings.

Figure 3:
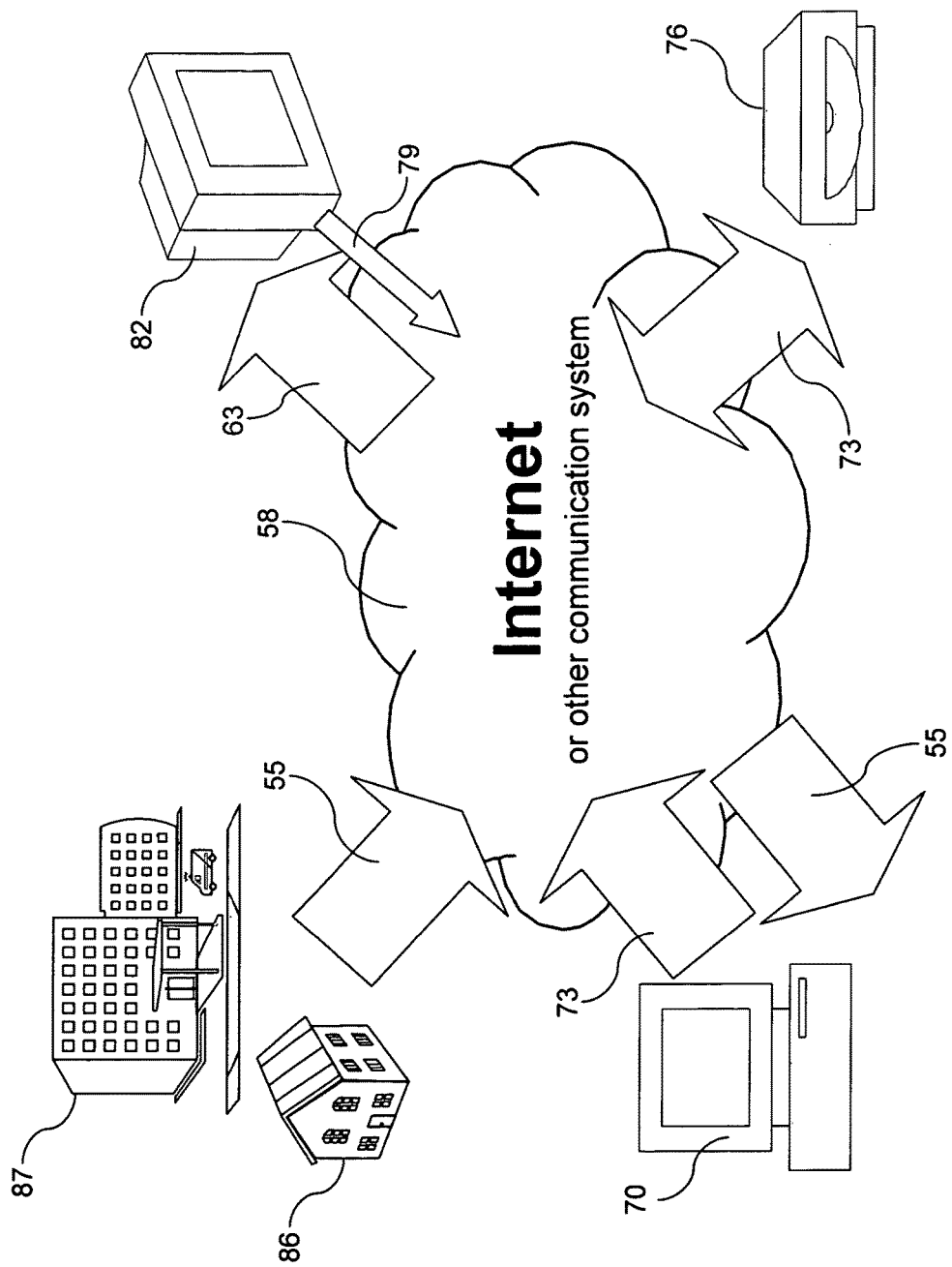
FIG. 3 Schematic diagram of the data transfer and sharing devices and/or processes of various embodiments of the present invention.

FIG. 3 is a schematic of one embodiment of the data acquisition device and system of the present invention. In FIG. 3, a data acquisition system is used to receive, filter, and optionally analyze signals from sensors (not shown) on a subject (not shown). The data acquisition system transmits a signal based, at least in part, on one or more of the signals from the sensors on the subject. The data acquisition device and system transmits the signal 55 from the subject's home 86, a hospital 87, or other location to a server 70 for analysis. The signal is transmitted over the internet or other communication system 58. The signal 55 that is transmitted over the internet or other communication system 58 can be compressed to provide better resolution or greater efficiency. The server 70 in this embodiment may also perform data analysis (not shown). The analyzed data 73 is then entered into a database 76. The analyzed data 73 in the database 76 can then be requested 79 and sent 63 to review stations 82 anywhere in the world via the internet or other communication system 58 for further analysis and review by clinicians, technicians, researchers, physicians and the like. The communications systems used for data transmission need not be the same at all stages. For example, a cellular network can be used to transmit data between the subject's home 86 and the remote analysis server 70. The internet can then be used to transmit data between the remote analysis server 70 and the database 76. Finally, in this example, a LAN could be used to transmit data between the database 76 and a review station 82.

Figure 4:
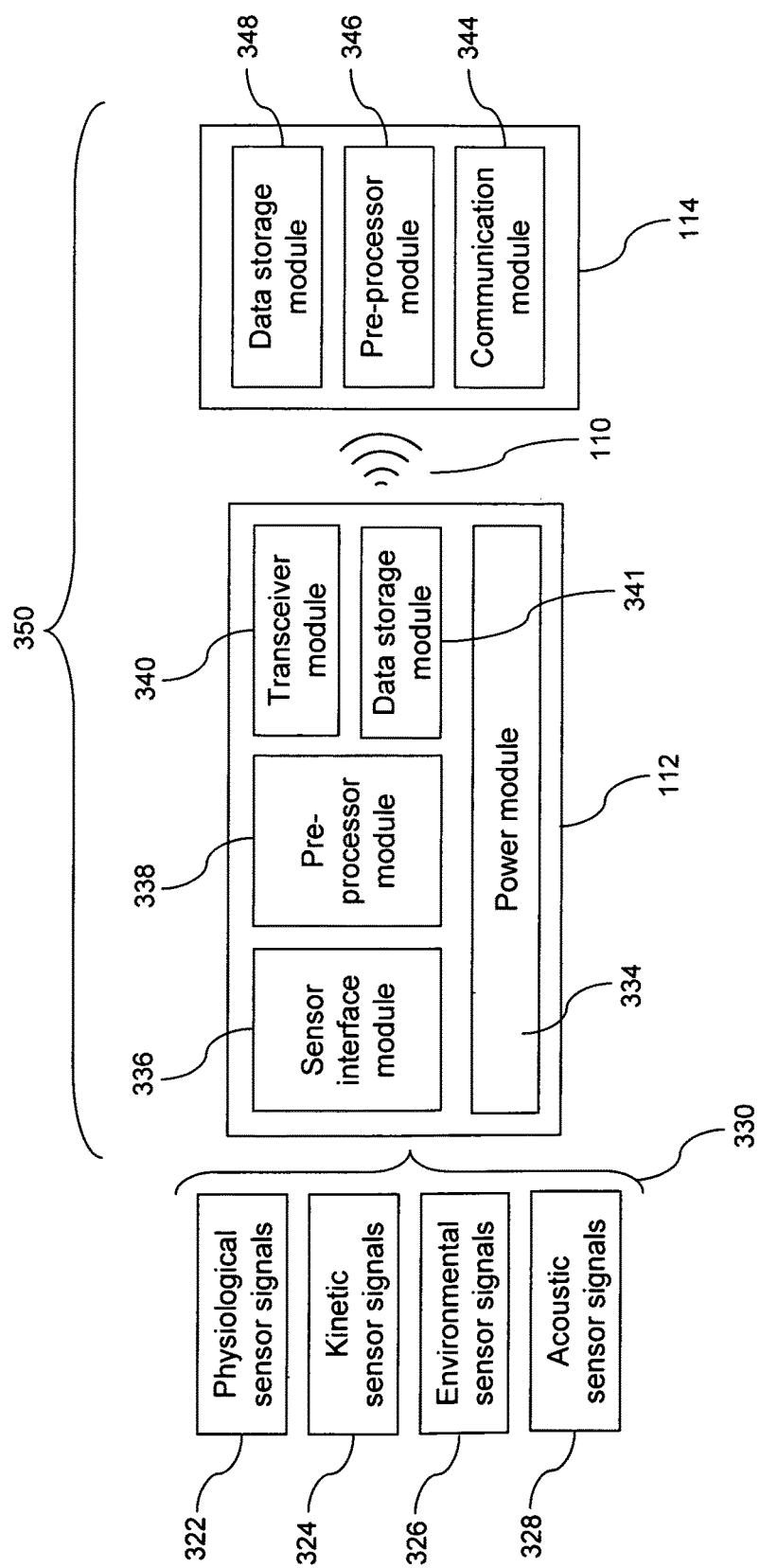
FIG. 4 Block diagram of one embodiment of the data acquisition system used in various embodiments of the present invention.

FIG. 4 is a block diagram showing the data flow through one embodiment of the data acquisition system 350 used in certain embodiments of the present invention. In this embodiment, various sensors generate physiological signals 322, kinetic signals 324, environmental signals 326, and acoustic signals 328. The sensor signals 330 are input into the data acquisition system 350, consisting of (a) a data acquisition device 112 containing a sensor interface module 336, a preprocessor module 338, a transceiver module 340, a data storage module 341, and a power module 334, and (b) a base station 114 containing a storage module 348, a second pre-processor module 346, and a communication module 344. Typically, the data acquisition device 112 is worn by the subject during the test period. For portability of the data acquisition device 112, the power module 334 can be battery-powered. The data acquisition device 112 sends data via wireless signal 110 to the base station 114. The base station 114 uses the communication module 344 to retransmit the signals from the sensors 330 and/or transmit signals based at least in part on at least one of the signals to remote stations (not shown). Optionally, all sensor signals 330 could be channeled directly into the data storage module 341 of the data acquisition device 112 and saved for download and analysis at a later time, eliminating the need for wireless transmission of data 110 to the base station 114. Further optionally, all sensor signals 330 could be directed into the data storage module 341 and saved for later download while simultaneously being transmitted to a remote station (not shown) via wireless communication 110 with the base station 114. Although transmission between the data acquisition device 112 and the base station 114 is shown in FIG. 4 as wireless 110, the connection could also be a wired connection in other embodiments of the data acquisition system.

Figure 5:
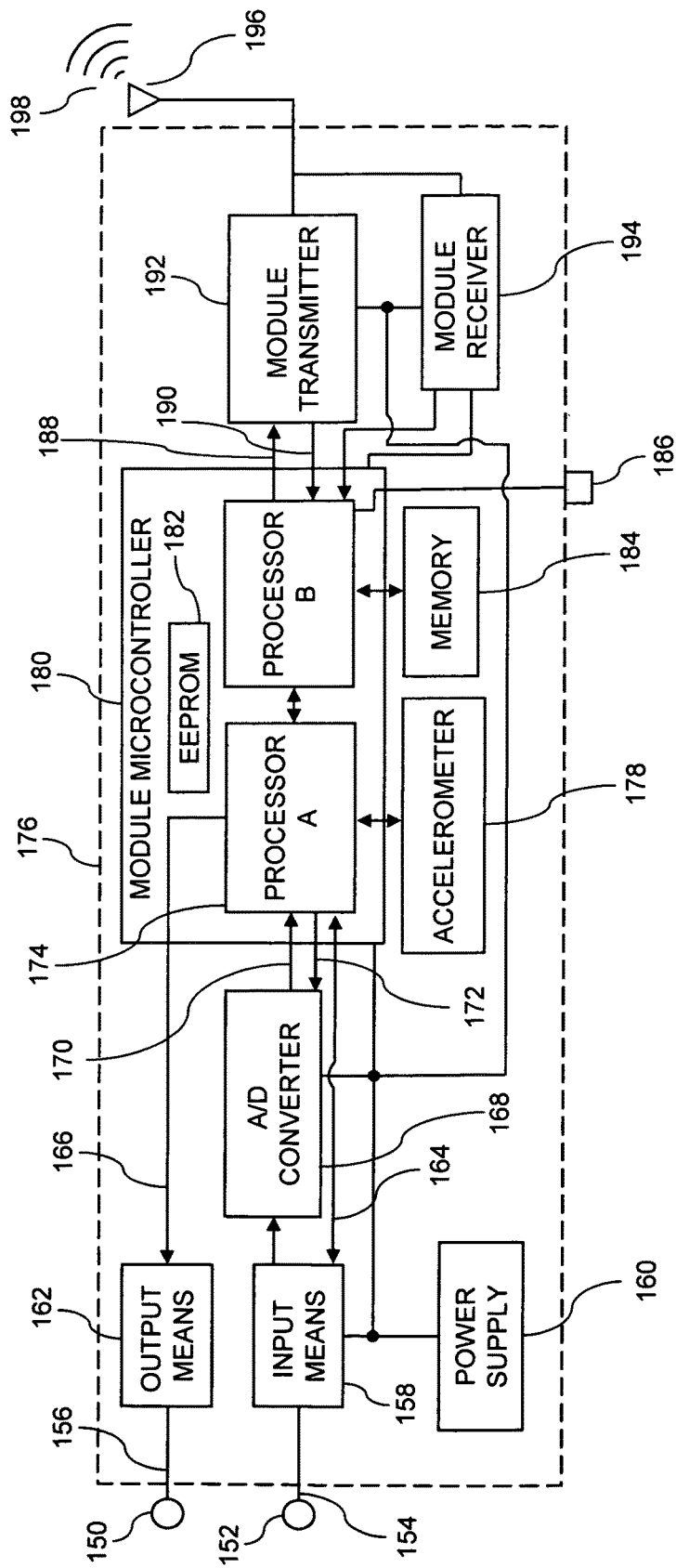
FIG. 5 Block diagram illustrating one embodiment of another data acquisition and data handling device and processes used in various embodiments of the present invention.

Referring now to FIG. 5, there is shown a more detailed block diagram of the signal processing module 176 of the data acquisition device (shown in FIG. 4) with the sensor or sensors 152 and the module antenna 196. The signal processing module 176 comprises input means 158, analog-to-digital (A/D) means 168, a module microcontroller 180 with a nonvolatile memory, advantageously, an EEPROM 182, a module transmitter 192, a connection to removable memory 184, a module receiver 194 and a module power supply 160 and output means 162. Although the module antenna 196 is shown externally located from the signal processing module 176, it can also be incorporated therein. A module power supply 160 provides electrical power to the signal processing module 176. Additionally the signal processing module 176 will preferably contain an accelerometer 178 connected to a microprocessor 174 for position detection, motion detection, and motion artifact correction.

The input means 158 is adjustable either under control of the module microcontroller 180 or by means of individually populatable components based upon the specific external input 154 (i.e. a signal from any sensor) characteristics and range enabling the input means 158 to accept that specific external input 154.

After receipt by the input means 158, the external input 154 is inputted to the A/D means 168. The A/D means 168 converts the input to a digital signal 170 and conditions it. The A/D means 168 utilizes at least one programmable A/D converter. This programmable A/D converter may be an AD7714 as manufactured by Analog Devices or similar. Depending upon the application, the input means 158 may also include at least one low noise differential preamp. This preamp may be an INA126 as manufactured by Burr-Brown or similar. The module microcontroller 180 can be programmed to control the input means 158 and the A/D means 168 to provide specific number of external inputs 154, sampling rate, filtering and gain. These parameters are initially configured by programming the module microcontroller 180 to control the input means 158 and the A/D means 168 via input communications line 164 and A/D communications line 172 based upon the input characteristics and the particular application. If different sensors are used, the A/D converter is reconfigured by reprogramming the module microcontroller 180.

The module microcontroller 180 controls the operation of the signal processing module 176. In the present embodiment, the module microcontroller 180 includes a serial EEPROM 182 but any nonvolatile memory (or volatile memory if the signal processing module remains powered) can be used. The EEPROM 182 can also be a separate component external to the module microcontroller 180. The module microcontroller may advantageously contain two microprocessors in series as shown in FIG. 5. The module microcontroller 180 is programmed by the external programming means (shown in FIG. 1) through the connector 186 or through radio frequency signal from the base station (shown in FIG. 1). The same module microcontroller 180, therefore, can be utilized for all applications and inputs by programming it for those applications and inputs. If the application or inputs change, the module microcontroller 180 is modified by merely reprogramming. The digital signal 170 is inputted to the module microcontroller 180. The module microcontroller 180 formats the digital signal 170 into a digital data stream 188 encoded with the data from the digital signal 170. The digital data stream 188 is composed of data bytes corresponding to the encoded data and additional data bytes to provide error correction and housekeeping functions. The digital data stream 188 is used to modulate the carrier frequency generated by the transmitter 192.

The module transmitter 192 is under module microcontroller 180 control. The module transmitter 192 employs frequency synthesis to generate the carrier frequency. In the preferred embodiment, this frequency synthesis is accomplished by a voltage controlled crystal reference oscillator and a voltage controlled oscillator in a phase lock loop circuit. The digital data stream 188 is used to frequency modulate the carrier frequency resulting in the wireless data transmission signal 198 which is then transmitted through the module antenna 196. The generation of the carrier frequency is controlled by the module microcontroller 180 through programming in the EEPROM 182, making the module transmitter 192 frequency agile over a broad frequency spectrum. In the United States and Canada a preferred operating band for the carrier frequency is 902 to 928 MHz. The EEPROM 182 can be programmed such that the module microcontroller 180 can instruct the module transmitter 192 to generate a carrier frequency in increments between 902 to 928 MHz. as small as about 5 to 10 kHz. In the US and other countries of the world, the carrier frequency may be in the 902-928 MHz, Wireless Medical Telemetry Bands (WMTS), 608-614 MHz, 1395-1400 MHz, or 1429-1432 MHz or other authorized band. This allows the system to be usable in non-North American applications and provides additional flexibility.

The voltage controlled crystal oscillator (not shown) in the module transmitter 192, not only provides the reference frequency for the module transmitter 192 but, advantageously also provides the clock function 190 for the module microcontroller 180 and the A/D means 168 assuring that all components of the signal processing module 176 are synchronized. An alternate design can use a plurality of reference frequency sources where this arrangement can provide certain advantages such as size or power consumption in the implementation. The module receiver 194 in the signal processing module 176 receives RF signals from the base station (shown in FIG. 1). The signals from the base station can be used to operate and control the signal processing module 176 by programming and reprogramming the module microcontroller 180 and EEPROM 182 therein.

The signal processing module 176 of the data acquisition device (shown in FIG. 1) also includes an output means 162 for sending analog and/or digital signals to various sensors or external devices 150. The output means receives signals and/or information 166 from the module microcontroller 180 and outputs 156 the signal to the sensor or external device 150. In an optional embodiment, communication between the module microcontroller 180 and the output means 162 is first passed through the A/D converter 168 to convert the digital signal from the module microcontroller 180 to an analog signal for use with sensors or external devices 150.

Figure 6:
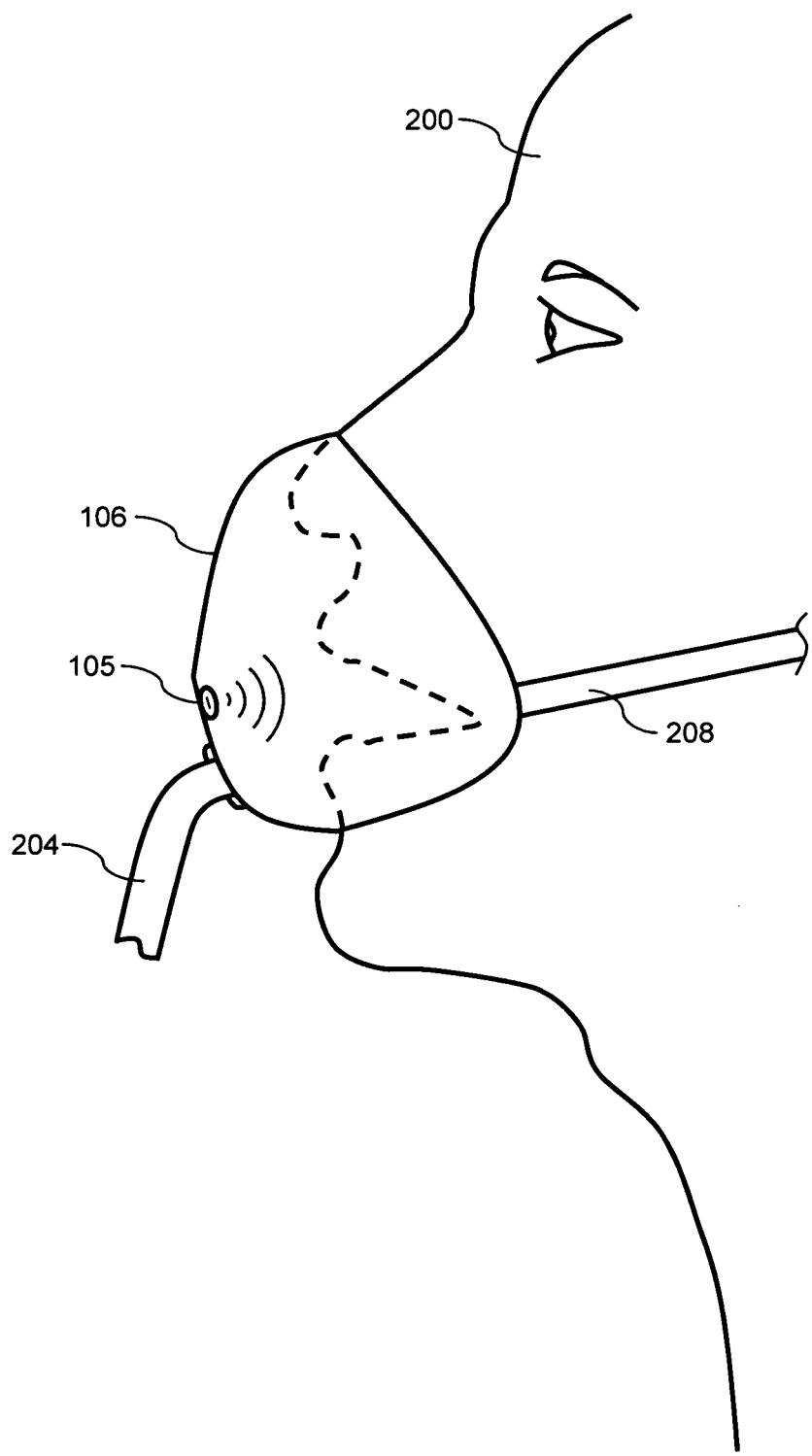
FIG. 6 Partial side view of a subject wearing a mask with acoustic transducer used in one embodiment of the present invention.

FIG. 6 is a schematic showing a subject 200 wearing one embodiment of the mask 106 used in the present invention to position the acoustic transducer 105 near the subject's mouth. The mask 106 shown here includes means 204 whereby the mask may be connected to a positive airway pressure device. Because of this, the mask can be simultaneously used to collect acoustic information on the state of the subject's airway and supply a positive pressure for positive airway pressure titration procedures. The mask is held tightly over the subject's mouth and nose by a strap 208 used to secure the mask to the subject 200. The mask 106 shown in FIG. 6 is preferably used during a positive airway pressure titration procedure in which acoustic data collected using the acoustic transducer 105 is used, at least in part, to quantify the effectiveness of the titration procedure and plan future treatment/intervention on behalf of the patient. Acoustic data collected using this embodiment can be stored and/or analyzed using the data acquisition system of the present invention (not shown) or, optionally, stored and/or analyzed using a specialized positive airway pressure device capable or performing such functions (not shown).

Figure 7:
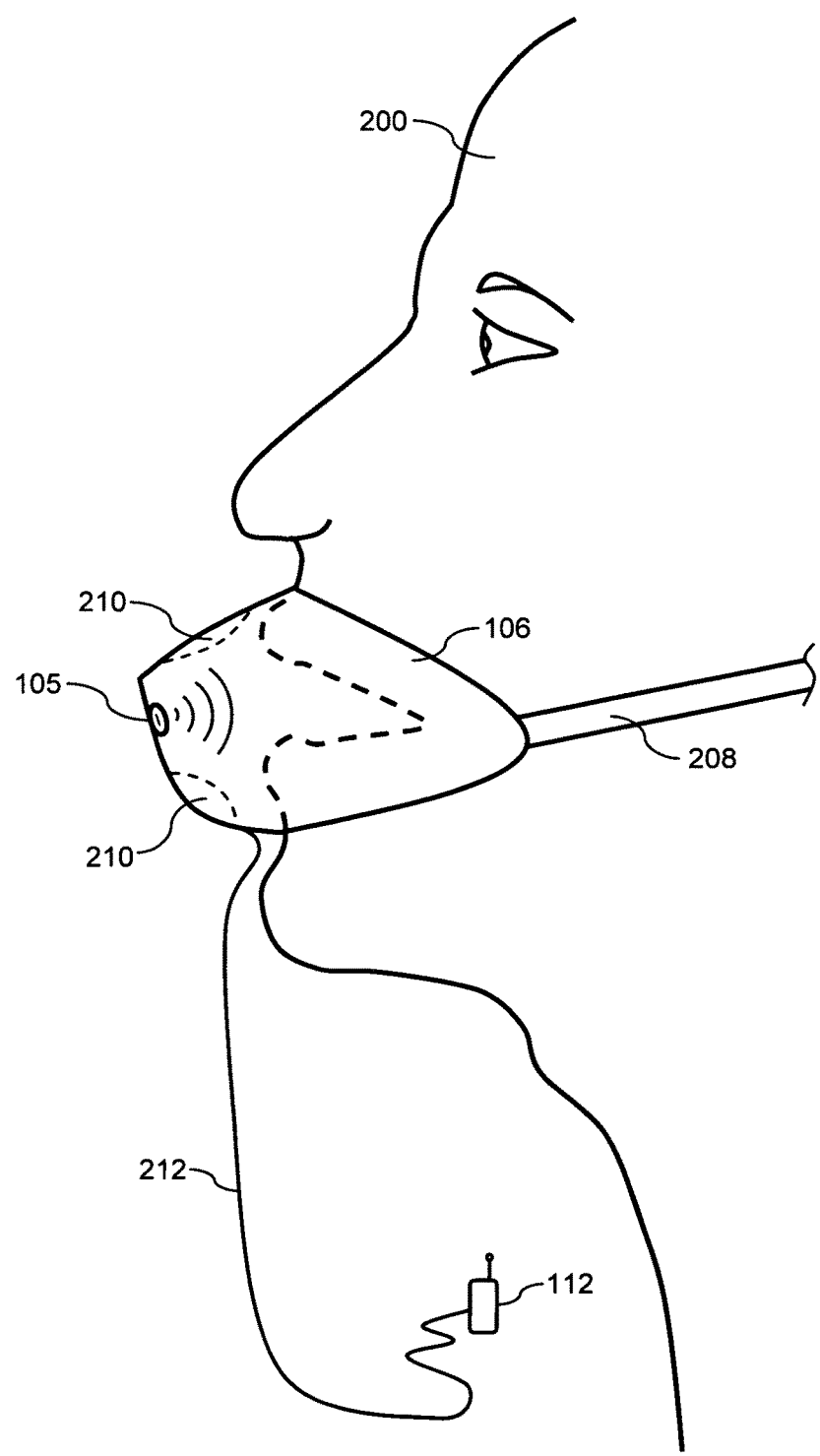
FIG. 7 Partial side view of a subject wearing a mask with acoustic transducer used in another embodiment of the present invention.

FIG. 7 shows another embodiment of the present invention wherein the mask 106 used to support and position the acoustic transducer 105 near the mouth of the subject 200 is an oral mask, covering only the mouth of a subject. In this embodiment, air ports 210 are placed in the mask to allow the subject 200 to breathe while wearing the mask. The mask is held tightly over the subject's mouth by a strap 208 used to secure the mask to the subject 200. As shown here, generation/recording of sound waves emitted into the subject's airway is transmitted to the data acquisition device 112 by a hard-wired connection 212. Storage and/or analysis of acoustic data can then be conducted either by the data acquisition device 112 or acoustic data can be further transferred by the data acquisition device 112 to other components of the data acquisition system for storage and/or analysis (shown in FIG. 1).

Figure 8:
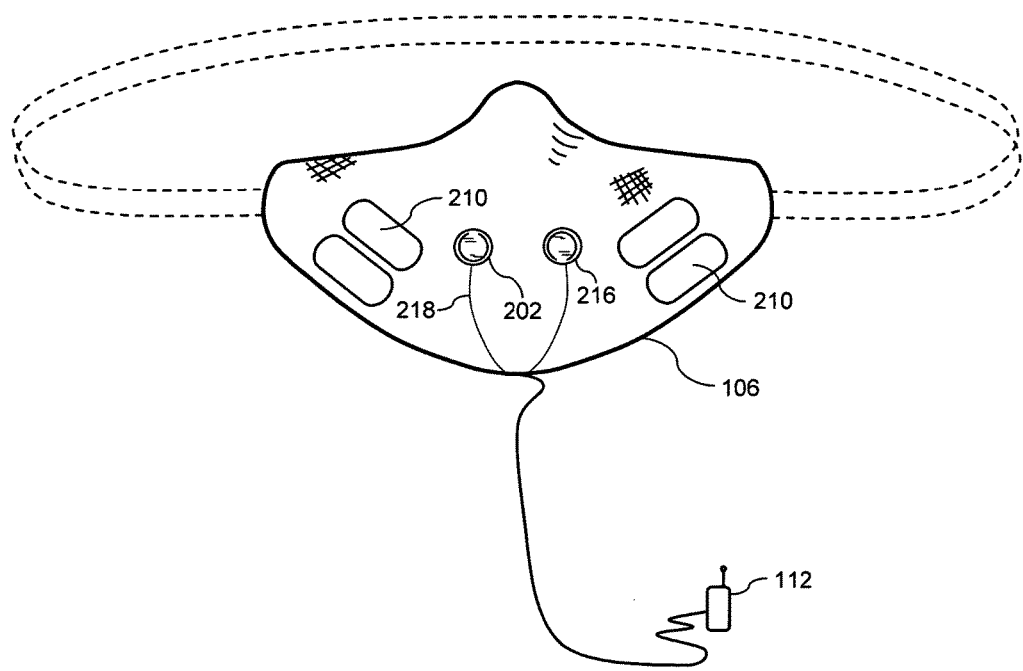
FIG. 8 Front view of one embodiment of a mask used with the present invention wherein the mask includes an independent acoustic generator and acoustic sensor.

Referring now to FIG. 8, there is shown a front view of one embodiment of the mask 106 used in certain embodiments of the present invention. Here, a separate acoustic sensor 202 and acoustic generator 216 are used to conduct acoustic analysis of a subject's airway. Wires 218 used to connect the acoustic sensor 202 and acoustic generator 216 to the data acquisition device 112 can be embedded in the mask (as shown here) or attached simply to the acoustic sensor and acoustic generator while not embedded in the mask. Though not shown here, in one envisioned embodiment, the acoustic sensor and acoustic generator are preferably secured in the mask in such a way that they can be easily removed and replaced with sensors and or generators of a different type but similar dimensions for use under varying conditions or applications. The mask 106 shown in FIG. 8 includes air ports 210 to allow for relatively unhindered breathing by the subject, while the mask is worn. Optionally, however, the mask could just as easily include a means of connection to a positive airway pressure device in place of air ports for applications involving the use of a positive airway pressure therapy.

Figure 9A:
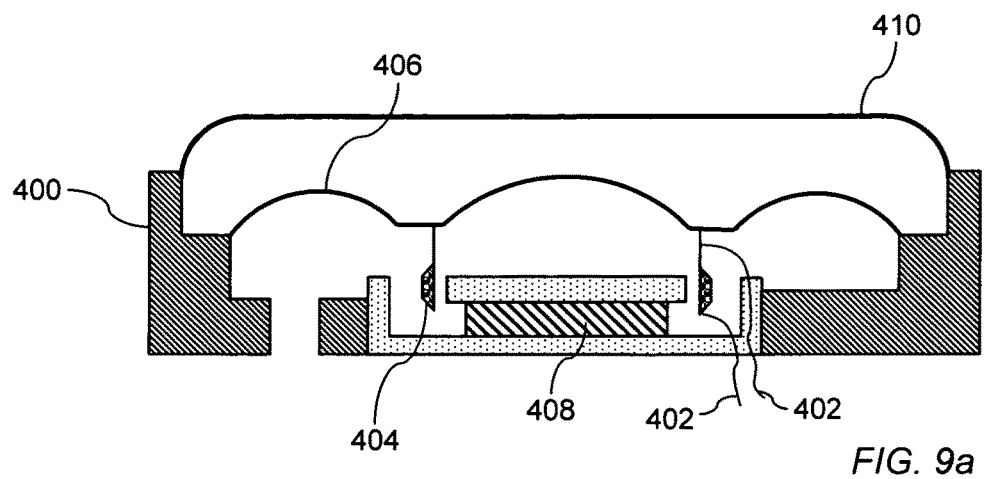
Figure 9B:
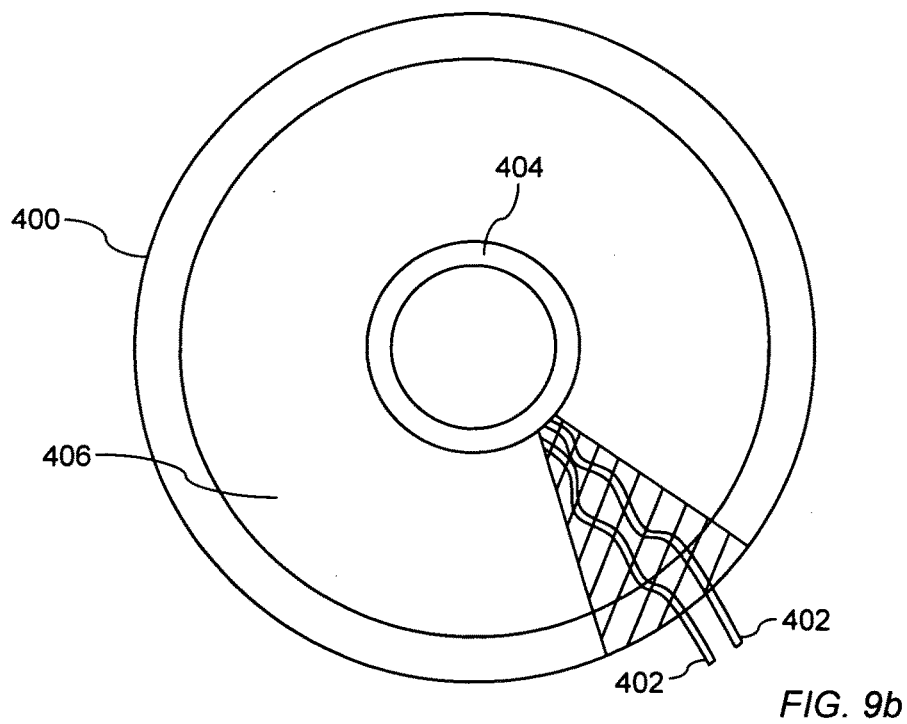

In FIG. 9 is shown a cross-sectional view FIG. 9a and a top view FIG. 9b of one example of a micro electro-acoustic transducer 400 which could be used in the present invention as an acoustic sensor, acoustic generator, or both. The acoustic transducer 400 is protected by a protective cover 410. The acoustic transducer 400 generates sound in response to a driving signal applied to the lead wires 402. When an alternating driving signal is applied, the moving coil 404 generates an alternating magnetic field which interacts with a non-alternating magnetic field created by the permanent magnet 408, causing the vibration plate 406 connected to the moving coil 404 to vibrate at the driving frequency, creating sound waves. When used as a sensor, magnetic flux through the moving coil 404 is measured at the lead wires as sound impinges on the vibration plate, causing it to vibrate at the frequency of the incoming sound. Thus, by producing a short generating pulse followed by a measurement of the pulse as it is reflected, the acoustic transducer 400 can serve as both an acoustic sensor and acoustic generator.

Figure 10A:
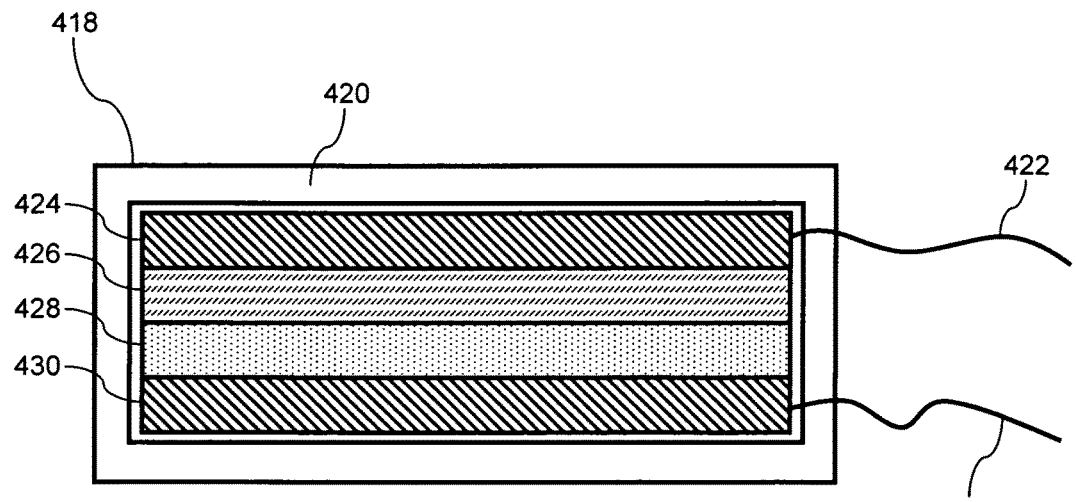
Figure 10B:
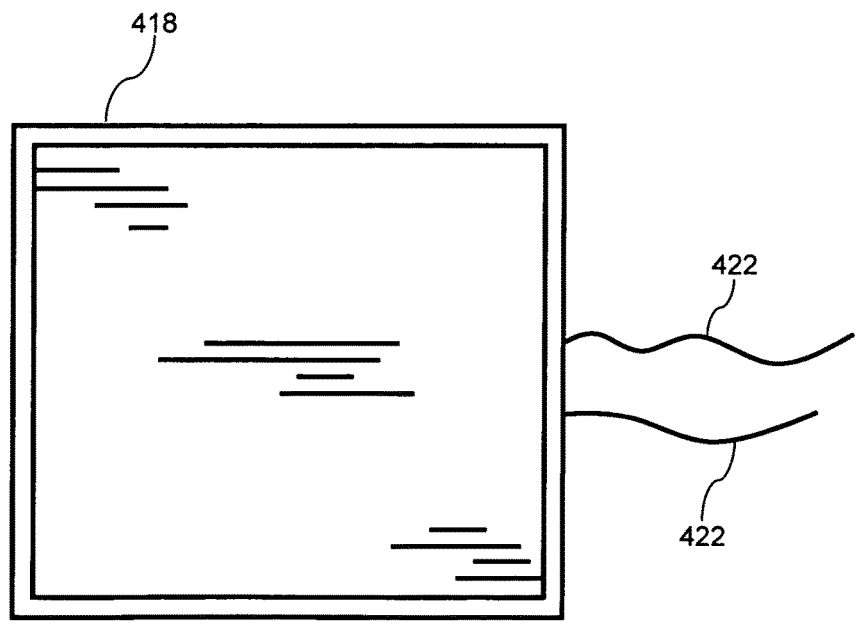

FIG. 10 shows a cross-sectional view FIG. 10a and a top view FIG. 10b of one example of a micro piezoelectric acoustic transducer 418 which could be used in the present invention as an acoustic sensor, acoustic generator, or both. In FIG. 10, a piezo crystal 426 is situated between two conductive metal layers 424, 430 which can, optionally, be attached to the piezo crystal 426 by a conductive glue 428. The piezoelectric acoustic transducer 418 is protected by a protective covering 420. When used as an acoustic sensor, sound waves impinging on one face of the piezo crystal 426, cause the piezo crystal to become distorted, producing electrical signals which are transferred by the conductive metal layers 424, 430 and lead wires 422 to an appropriate detection apparatus allowing recording of sound waves. In an opposite manner, by supplying an electrical signal to the lead wires 422 the piezo crystal 426 can be caused to vibrate, producing sound waves.

Figure 11:
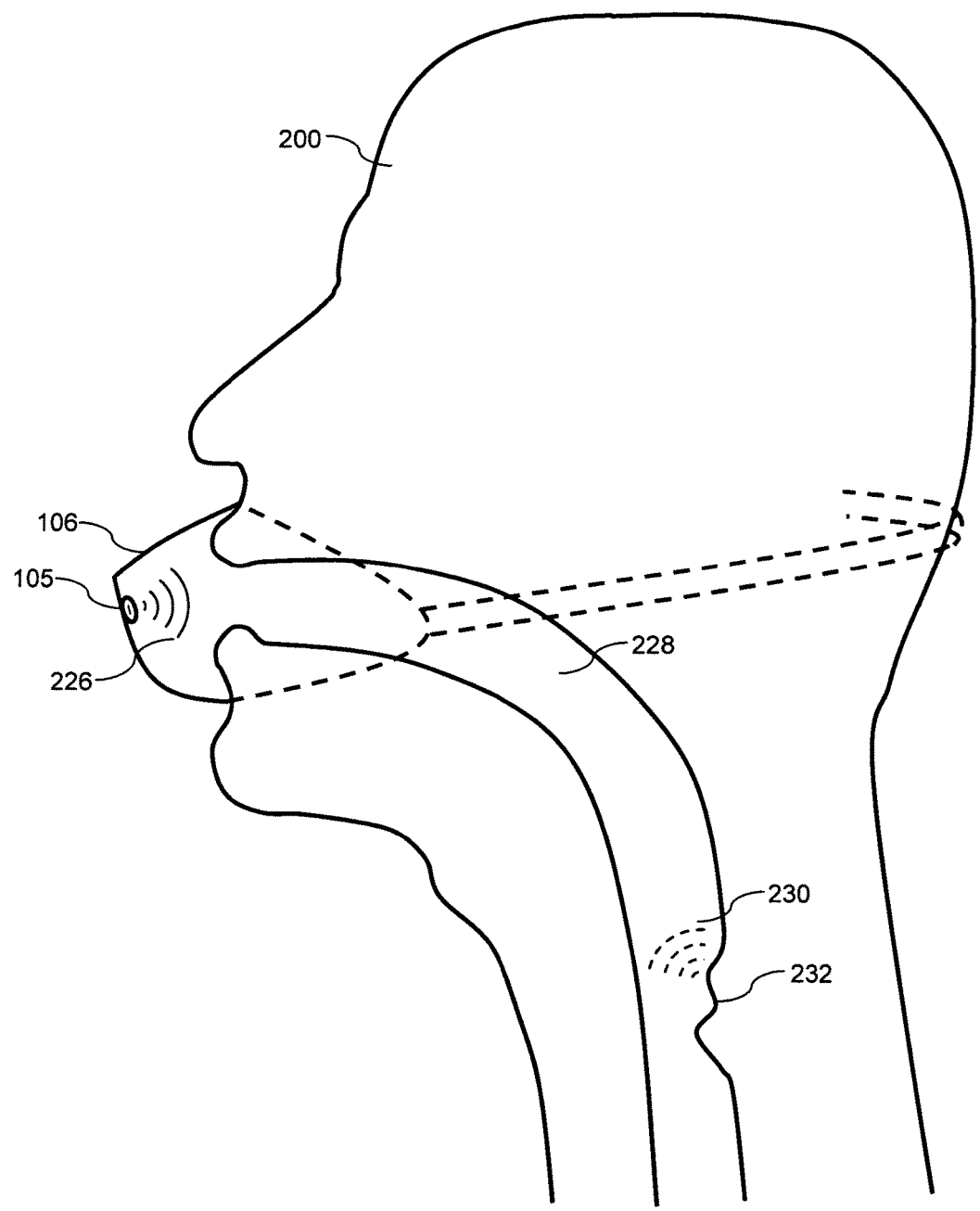
FIG. 11 Full cross-sectional schematic view of a subject using one embodiment of the present invention demonstrating the use of (acoustical) sound waves to examine the subject's airway.

FIG. 11 is a cross-sectional view of a subject 200 wearing one embodiment of the mask 106 used in the present invention. In FIG. 11, sound waves 226 are applied to the subject's airway 228 using an acoustic transducer 105. As the sound waves 226 travel down the subject's airway 228, they may be reflected as they contact obstruction(s) 232 present in the subject's airway. The reflected waves 230 are then measured using the acoustic transducer 105. Through subsequent analysis of certain properties of the reflected waves 230, information concerning location, morphology, and dynamic of the obstruction(s) 232 can be obtained and used in diagnosis and/or treatment of the subject's sleep respiratory disorder.

Figure 12:
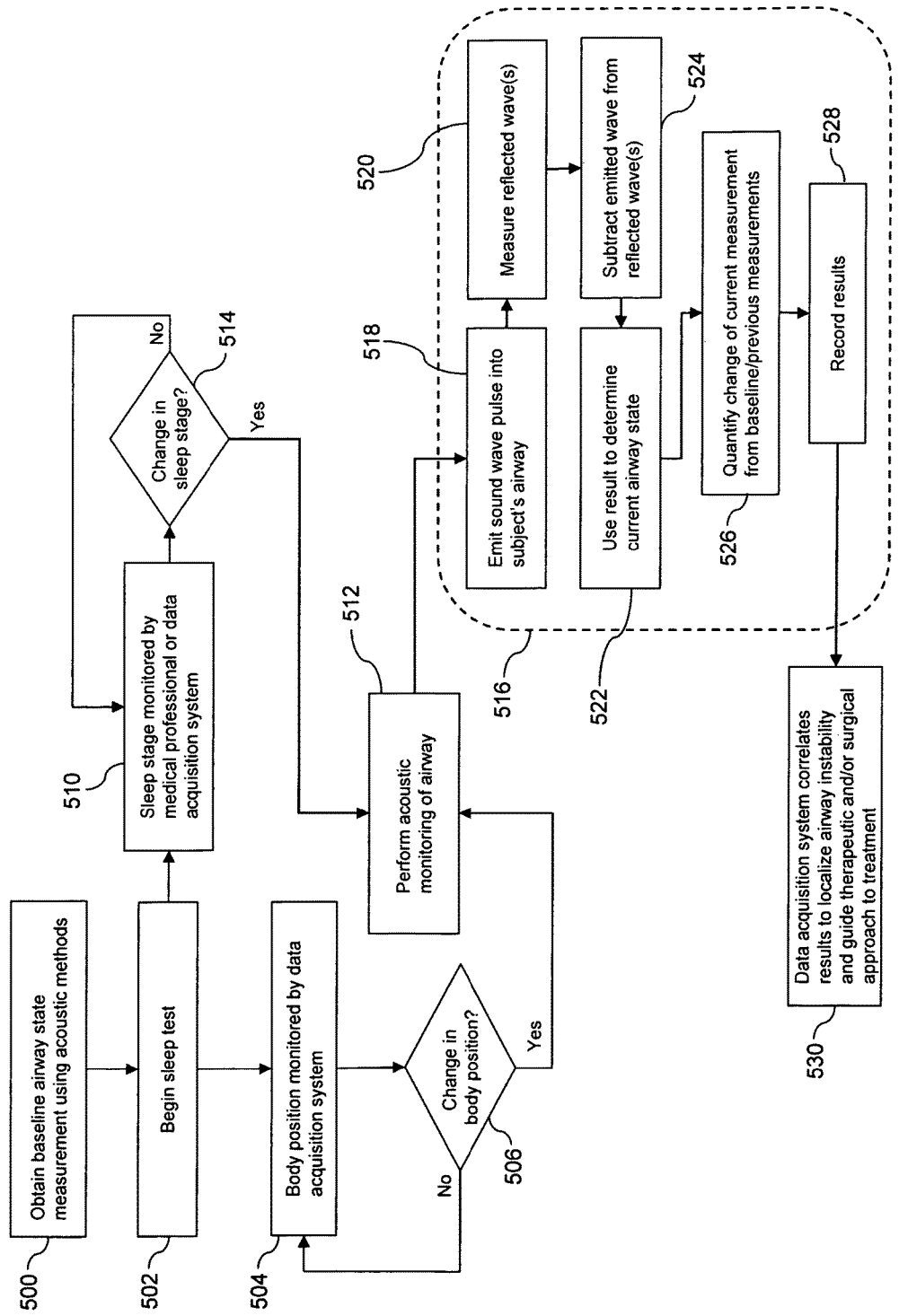
FIG. 12 Flow diagram illustrating one embodiment of the method of the present invention.

FIG. 12 is a flow diagram depicting the steps and/or processes implemented in one embodiment of the present invention, particularly during a diagnostic sleep test. In this approach, a baseline acoustic analysis of the state of a subject's airway is performed 500 in order to provide a reference for acoustic measurements obtained while the subject sleeps. Preferably, the baseline or reference measurement is obtained while the subject is in a supine, or other common sleeping position. After beginning the sleep test 502, both sleep stage and body position are monitored by the data acquisition system and/or a medical professional 504, 510. Monitoring of sleep stage and body position can be performed by various means. Sleep stage can be monitored either electronically by one or various components of the data acquisition system (e.g. the data acquisition device, external programming and analysis device, or both), or by a medical professional trained to recognize changes in sleep stage. If a change in sleep stage is detected either electronically, or by a medical professional 514, the command is sent to the data acquisition system to perform acoustic monitoring and analysis of the state of a subject's airway 512. Body position can be monitored by any of the various methods described above. For example, a change in body position may be detected by the data acquisition system using an accelerometer or gyroscope attached to the subject. Upon detection of a change in body position 506, the data acquisition system is given the command to conduct acoustic analysis and monitoring of the patient's airway 512, triggering the same process as would occur if a change in sleep stage were observed.

Acoustic monitoring and analysis of a subject's airway 516 is comprised of several steps which can be controlled or modulated by one or various components of the data acquisition system. Upon initiation of the acoustic monitoring process, a sound wave pulse is emitted into the subject's airway 518. Reflected waves from the sound pulse are then measured 520 using the acoustic transducer 105 (FIG. 1), and the difference between the original emitted wave and the reflected wave is calculated 524 to provide information on the change in airway state between the current measurement and previous measurement(s) 522. Change from previous acoustic measurements is then calculated 526 and the results recorded 528 for use in subject diagnosis. Using various methods and algorithms, the data acquisition system then correlates the results of all acoustic measurements 530 performed during the sleep test to provide information on, among other things, the location, morphology, and dynamic of the tissue causing sound reflection. This information is then used to and guide therapeutic or surgical intervention on behalf of the subject 530.

Figure 13:
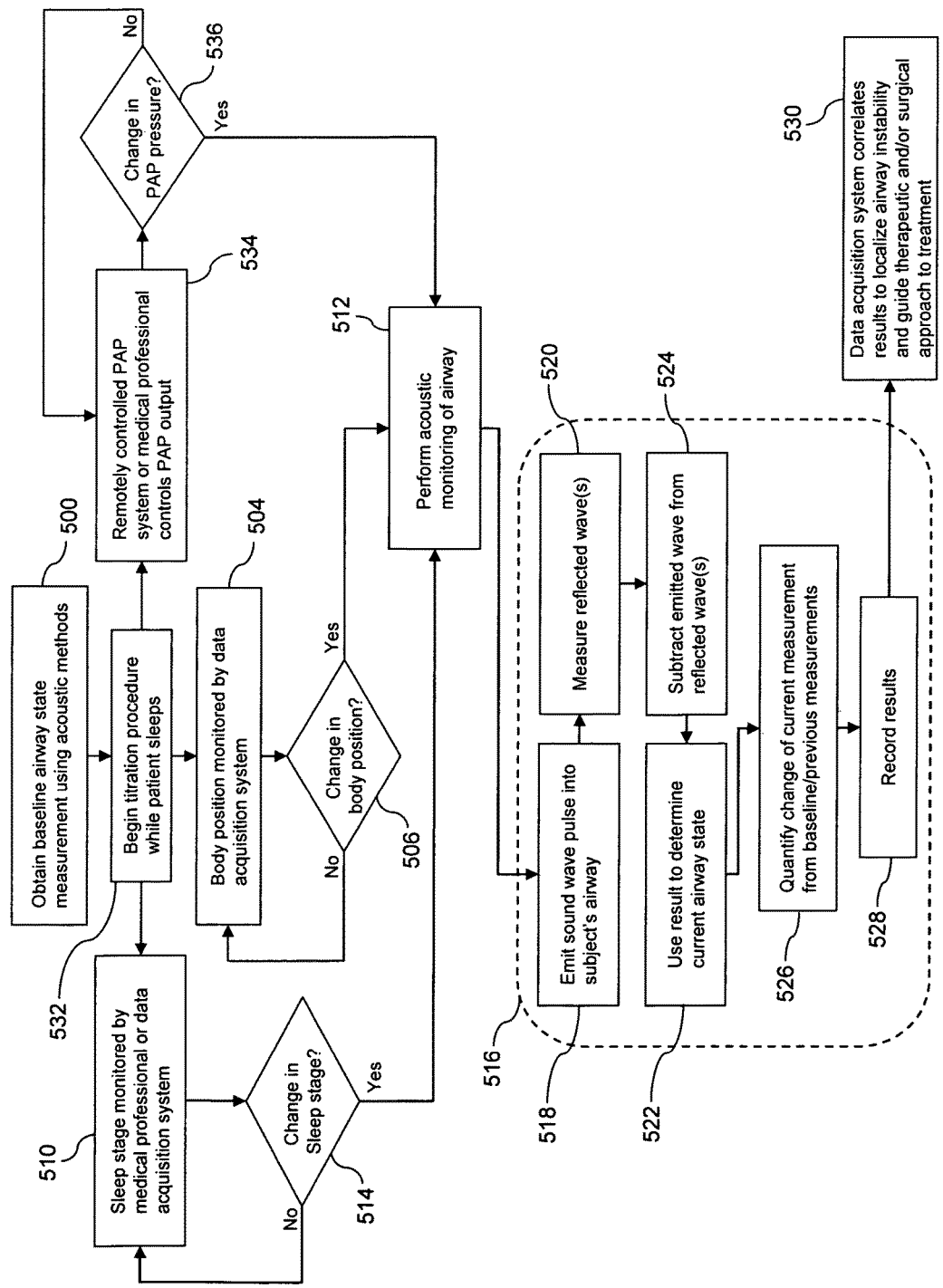
FIG. 13 Flow diagram illustrating another embodiment of the method of the present invention.

FIG. 13 is a flow diagram depicting the steps and/or processes implemented in one embodiment of the present invention, particularly during a positive airway pressure titration procedure. In this approach, a baseline acoustic analysis of the state of a subject's airway is performed 500 in order to provide a reference for acoustic measurements obtained while the subject sleeps. Preferably, the baseline or reference measurement is obtained while the subject is in a supine, or other common sleeping position. After beginning the titration procedure 532, both sleep stage and body position are monitored by the data acquisition and/or a medical professional 510, 504 as described above. In addition, positive airway pressure (PAP) output is monitored and controlled by a remotely controlled PAP system or a medical professional 534. If PAP pressure is monitored by a remotely controlled PAP system, it is preferably performed as shown in FIG. 2 wherein a treatment interface device 126 (FIG. 2) is used to control/communicate between the PAP device and other components of the data acquisition system. In this embodiment, if a change in PAP pressure is detected 536 either electronically, or by a medical professional, the command is sent to the data acquisition system to perform acoustic monitoring and analysis of the state of a subject's airway 512 as described above. By correlating PAP pressure with both body position and sleep stage during the titration procedure, greater insight is gained into the subject's sleep disorder. Additionally, change in PAP pressure can be adjusted based, at least in part, on acoustic monitoring results, as shown in greater detail in FIG. 14.

Figure 14:
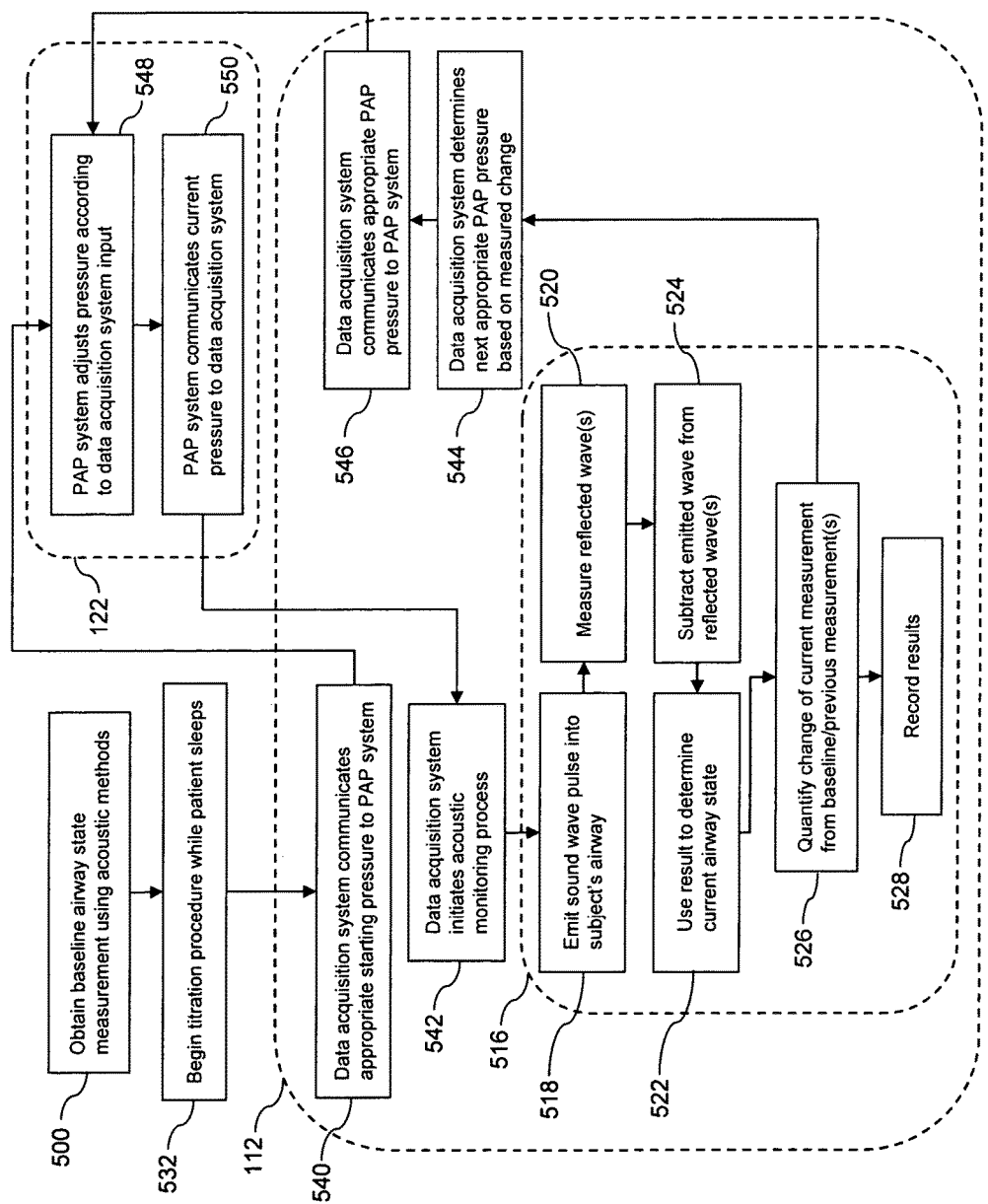
FIG. 14 Flow diagram illustrating still another embodiment of the method of the present invention.

FIG. 14 is a flow diagram depicting, in greater detail, the steps and/or processes which occur when PAP titration is conducted using a PAP system capable of communication with other components of the data acquisition system. After obtaining a baseline acoustic measurement 500 and beginning the titration procedure 532 as described above, the data acquisition system, represented here by box 112, communicates an appropriate starting pressure to the PAP system 540. The PAP system, represented by box 122, then adjusts output pressure according to input from the data acquisition system 548 and communicates this change in pressure back to the data acquisition system 550. Upon confirmation of PAP pressure output, the data acquisition system initiates the acoustic monitoring process as described above, and represented by box 516. Based upon the change of the subject's airway state as measured by the acoustic monitoring and analysis process, the data acquisition system determines the next appropriate PAP pressure setting 544 and communicates this setting to the PAP 546. This pressure adjustment can be either an increase or decrease in pressure depending on the calculated change and occurs within certain preset maximum and minimum limits. Following this, the PAP system adjusts according to data acquisition system input 548, and the process is repeated again. The method illustrated in this embodiment is particularly useful in gaining understanding of the location and dynamic of obstructive tissue within a subject's airway because PAP pressure could be run dynamically through the set limits multiple times during a sleep titration test allowing greater resolution and understanding of the nature of the obstructive tissue causing a subject's sleep disorder.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What we claim is:

1. A method of diagnosing and treating sleep related airway obstructions of a subject comprising the steps of:
  conducting a sleep test using a data acquisition system comprising at least one actuator and at least one sensor, the at least one actuator being an acoustic generator and the at least one sensor being an acoustic sensor, the sleep test comprising the step of measuring or estimating a subject's airway for obstruction(s) during sleep with both the at least one actuator and at least one sensor of the data acquisition system, using the measured or estimated obstruction(s) in the subject's airway determined during the sleep test, at least in part, to make a determination of tissue to be removed or extracted during surgery, and performing surgery to remove, at least in part, the obstruction(s) identified at least in part by the sleep test.

2. The method of claim 1 wherein said data acquisition system is comprised of at least one additional sensor, the at least one additional sensor being a body position sensor, and wherein the measured or estimated obstruction(s) are correlated with the measured or estimated body position determined during the sleep test, at least in part, to make a determination of tissue to be removed or extracted during surgery.

3. The method of claim 1 wherein said data acquisition system is comprised of at least one additional sensor, the at least one additional sensor for determining the subject's sleep stage, and wherein the measured or estimated obstruction(s) are correlated with the measured or estimated sleep stage determined during the sleep test, at least in part, to make a determination of tissue to be removed or extracted during surgery.

4. The method of claim 1 wherein said data acquisition system is comprised of at least one additional sensor, the at least one additional sensor being used to measure or estimate sleep respiratory events, and wherein the measured or estimated obstruction(s) are correlated with the measured or estimated sleep respiratory events determined during the sleep test, at least in part, to make a determination of tissue to be removed or extracted during surgery.

5. The method of claim 1 wherein said data acquisition system is comprised of at least three additional sensors, the at least three additional sensors being used to measure or estimate body position, sleep stage, and sleep respiratory events, and wherein the measured or estimated obstruction(s) are correlated with the measured or estimated body position, sleep stage, and sleep respiratory events determined during the sleep test, at least in part, to make a determination of tissue to be removed or extracted during surgery.

6. The method of claim 1 wherein said data acquisition system is comprised of at least three additional sensors for measuring physiological, kinetic, and/or environmental parameters pertaining to a subject's sleep quality.

7. A method of diagnosing and treating sleep related airway obstructions of a subject comprising the steps of:

conducting a sleep test using a data acquisition system comprising at least one actuator and at least one sensor, the at least one actuator being an acoustic generator and the at least one sensor being an acoustic sensor, the sleep test comprising the step of measuring or estimating a subject's airway for obstruction(s) during sleep with both the at least one actuator and at least one sensor of the data acquisition system, reviewing the sleep test to determine whether treatment is necessary or desired, conducting a second sleep test using the data acquisition system while titrating the subject with a PAP device to measure or estimate the effect of the PAP device on the subject's airway obstruction(s), and determining whether to continue having the subject use the PAP device or to perform surgery on the subject, based in part, on the measured or estimated effect of the PAP device on the subject's airway.

8. The method of claim 7 wherein said data acquisition system is comprised of at least one additional sensor, the at least one additional sensor being a body position sensor, and wherein determining whether to continue having the subject use the PAP device or to perform surgery on the subject is based, at least in part, on the measured or estimated effect of the PAP device on the subject's airway correlated with the subject's measured or estimated body position.

9. The method of claim 7 wherein said data acquisition system is comprised of at least one additional sensor, the at least one additional sensor for determining a subject's sleep stage, and wherein determining whether to continue having the subject use the PAP device or to perform surgery on the subject is based, at least in part, on the measured or estimated effect of the PAP device on the subject's airway correlated with the subject's measured or estimated sleep stage.

10. The method of claim 7 wherein said data acquisition system is comprised of at least one additional sensor, the at least one additional sensor being used to measure or estimate sleep respiratory events, and wherein determining whether to continue having the subject use the PAP device or to perform surgery on the subject is based, at least in part, on the measured or estimated effect of the PAP device on the subject's airway correlated with the subject's measured or estimated sleep respiratory event(s).

11. The method of claim 7 wherein said data acquisition system is comprised of at least three additional sensors, the at least three additional sensors being used to measure or estimate body position, sleep stage, and sleep respiratory events, and wherein determining whether to continue having the subject use the PAP device or to perform surgery on the subject is based, at least in part, on the measured or estimated effect of the PAP device on the subject's airway correlated with the subject's measured or estimated body position, sleep stage and sleep respiratory event(s).

12. The method of claim 7 wherein said data acquisition system is comprised of at least three additional sensors for measuring physiological, kinetic, and/or environmental parameters pertaining to a subject's sleep quality.

13. The method of claim 7 wherein said data acquisition system is capable of transmitting signals and/or information to said PAP device and, wherein said PAP device is capable of transmitting signals and/or information to said data acquisition system and, wherein communication of information between said data acquisition device and said PAP device is used to optimize effectiveness of said PAP device on the subject's airway obstructions and/or increase resolution of the location of the subject's airway obstructions.

* * * * *